US006602675B2

(12) United States Patent
Short et al.

(10) Patent No.: US 6,602,675 B2
(45) Date of Patent: Aug. 5, 2003

(54) HIGH THROUGHPUT SCREENING OF MYCELIA FOR BIOACTIVITIES OR BIOMOLECULES

(75) Inventors: Jay M. Short, Rancho Santa Fe, CA (US); Martin Keller, San Diego, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/848,083

(22) Filed: May 3, 2001

(65) Prior Publication Data

US 2001/0034040 A1 Oct. 25, 2001

Related U.S. Application Data

(60) Division of application No. 09/636,778, filed on Aug. 11, 2000, which is a continuation of application No. 09/098,206, filed on Jun. 16, 1998, now Pat. No. 6,174,673, which is a continuation-in-part of application No. 08/876,276, filed on Jun. 16, 1997.

(51) Int. Cl.$^7$ ............................................. G01N 33/569
(52) U.S. Cl. ......................... 435/7.32; 435/4; 435/7.4
(58) Field of Search ............................ 435/4, 7.32, 7.4

(56) References Cited

U.S. PATENT DOCUMENTS

| 4,399,219 A | 8/1983 | Weaver |
| 4,643,968 A | 2/1987 | Weaver |
| 4,647,536 A | 3/1987 | Mosbach et al. |
| 4,916,060 A | 4/1990 | Weaver |
| 4,959,301 A | 9/1990 | Weaver et al. |
| 5,055,390 A | 10/1991 | Weaver et al. |
| 5,225,332 A | 7/1993 | Weaver et al. |
| 6,057,103 A * | 5/2000 | Short |

FOREIGN PATENT DOCUMENTS

| WO | WO 96/34112 | 10/1996 |
| WO | WO 97/04077 | 2/1997 |
| WO | WO 97/20078 | 6/1997 |
| WO | WO 97/48717 | 12/1997 |
| WO | WO 98/56904 | 12/1998 |
| WO | WO 99/49315 | 9/1999 |
| WO | WO99/54494 | 10/1999 |

OTHER PUBLICATIONS

Roessner et al., "Fluorescence–Based Method for Selection of Recombinant Plasmids," *BioTechniques*, 19:760–764, Nov. 1995.
Wittrup et al., "Microencapsulation Selection for Isolation of Yeast Mutants with Increased Secretion of *Aspergillus awamori* Glucoamylase," *Biotechnology and Bioengineering*, 42(3):351–356, Jul. 1993.

* cited by examiner

*Primary Examiner*—James Ketter
*Assistant Examiner*—Bronwen M. Loeb
(74) *Attorney, Agent, or Firm*—Gray Cary Ware & Freidenrich, LLP; Lisa A. Haile

(57) ABSTRACT

Disclosed is a process for identifying clones having a specified activity of interest, which process comprises (i) generating one or more expression libraries derived from nucleic acid directly isolated from the environment; and (ii) screening said libraries utilizing a fluorescence activated cell sorter to identify said clones. More particularly, this is a process for identifying clones having a specified activity of interest by (i) generating one or more expression libraries derived from nucleic acid directly or indirectly isolated from the environment; (ii) exposing said libraries to a particular substrate or substrates of interest; and (iii) screening said exposed libraries utilizing a fluorescence activated cell sorter to identify clones which react with the substrate or substrates. Also provided is a process for identifying clones having a specified activity of interest by (i) generating one or more expression libraries derived from nucleic acid directly or indirectly isolated from the environment; and (ii) screening said exposed libraries utilizing an assay requiring co-encapsulation, a binding event or the covalent modification of a target, and a fluorescence activated cell sorter to identify positive clones.

10 Claims, 16 Drawing Sheets

β-Gal clone with different substrates

- cells were stained with FDG, CMFDG or C12FDG, incubated for 30 min. at 70°C, spotted onto a slide and exposed to UV light.
- bright spot indicates staining of cells

FDG

C12FDG

CMFDG

*Streptomyces lividans* mycelia      *Streptomyces "diversa"* Unicells

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence

```
<220> FEATURE:
<223> OTHER INFORMATION: oligonucleotide for PCR

<400> SEQUENCE: 1
agagtttgat cctggctcag                                           20

<210> SEQ ID NO 2
<211> LENGTH: 19
<212> TYPE: DNA
<213> ORGANISM: Artificial Sequence
<220> FEATURE:
<223> OTHER INFORMATION: oligonucleotide for PCR

<400> SEQUENCE: 2
ggttaccttg ttacgactt                                            19
```

HIGH THROUGHPUT SCREENING OF MYCELIA FOR BIOACTIVITIES OR BIOMOLECULES

This application is a divisional of U.S. patent application Ser. No. 09/636,778, filed Aug. 11, 2000, which is a continuation of U.S. patent application Ser. No. 09/098,206, filed Jun. 16, 1998 now U.S. Pat. No. 6,174,673, continuation-in-part of U.S. application Ser. No. 08/876,276, filed Jun. 16, 1997.

FIELD OF THE INVENTION

The present invention relates generally to the identification of new bioactive molecules and particularly to methods for recovering such molecules by co-encapsulation and fluorescence activated cell sorting (FACS).

BACKGROUND OF THE INVENTION

There is a critical need in the chemical industry for efficient catalysts for the practical synthesis of optically pure materials; enzymes can provide the optimal solution. All classes of molecules and compounds that are utilized in both established and emerging chemical, pharmaceutical, textile, food and feed, detergent markets must meet stringent economical and environmental standards. The synthesis of polymers, pharmaceuticals, natural products and agrochemicals is often hampered by expensive processes which produce harmful byproducts and which suffer from low enantioselectivity (Faber, 1995; Tonkovich and Gerber, U.S. Dept of Energy study, 1995). Enzymes have a number of remarkable advantages which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries (Faber, 1995). Enzyme-based processes have been gradually replacing many conventional chemical-based methods (Wrotnowski, 1997). A current limitation to more widespread industrial use is primarily due to the relatively small number of commercially available enzymes. Only ~300 enzymes (excluding DNA modifying enzymes) are at present commercially available from the >3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. Enzymes have evolved by selective pressure to perform very specific biological functions within the milieu of a living organism, under conditions of mild temperature, pH and salt concentration. For the most part, the non-DNA modifying enzyme activities thus far described (Enzyme Nomenclature, 1992) have been isolated from mesophilic organisms, which represent a very small fraction of the available phylogenetic diversity (Amann et al., 1995). The dynamic field of biocatalysis takes on a new dimension with the help of enzymes isolated from microorganisms that thrive in extreme environments. Such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge (Adams and Kelly, 1995). Enzymes obtained from these extremophilic organisms open a new field in biocatalysis.

For example, several esterases and lipases cloned and expressed from extremophilic organisms are remarkably robust, showing high activity throughout a wide range of temperatures and pHs. The fingerprints of five of these esterases show a diverse substrate spectrum, in addition to differences in the optimum reaction temperature. As seen in FIG. 1, esterase #5 recognizes only short chain substrates while #2 only acts on long chain substrates in addition to a huge difference in the optimal reaction temperature. These results suggest that more diverse enzymes fulfilling the need for new biocatalysts can be found by screening biodiversity. Substrates upon which enzymes act are herein defined as bioactive substrates.

Furthermore, virtually all of the enzymes known so far have come from cultured organisms, mostly bacteria and more recently archaea (Enzyme Nomenclature, 1992). Traditional enzyme discovery programs rely solely on cultured microorganisms for their screening programs and are thus only accessing a small fraction of natural diversity. Several recent studies have estimated that only a small percentage, conservatively less than 1%, of organisms present in the natural environment have been cultured (see Table I, Amann et al., 1995, Barns et. al 1994, Torvsik, 1990). For example, Norman Pace's laboratory recently reported intensive untapped diversity in water and sediment samples from the "Obsidian Pool" in Yellowstone National Park, a spring which has been studied since the early 1960's by microbiologists (Barns, 1994). Amplification and cloning of 16S rRNA encoding sequences revealed mostly unique sequences with little or no representation of the organisms which had previously been cultured from this pool. This suggests substantial diversity of archaea with so far unknown morphological, physiological and biochemical features which may be useful in industrial processes. David Ward's laboratory in Bozmen, Mont. has performed similar studies on the cyanobacterial mat of Octopus Spring in Yellowstone Park and came to the same conclusion, namely, tremendous uncultured diversity exists (Bateson et al., 1989). Giovannoni et al. (1990) reported similar results using bacterioplankton collected in the Sargasso Sea while Torsvik et al. (1990) have shown by DNA reassociation kinetics that there is considerable diversity in soil samples. Hence, this vast majority of microorganisms represents an untapped resource for the discovery of novel biocatalysts. In order to access this potential catalytic diversity, recombinant screening approaches are required.

The discovery of novel bioactive molecules other than enzymes is also afforded by the present invention. For instance, antibiotics, antivirals, antitumor agents and regulatory proteins can be discovered utilizing the present invention.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of one or more identical members. Clustering is a prerequisite for maintaining identity between genes, although clustered genes are not necessarily identical. Gene clusters range from extremes where a duplication is generated of adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. As indicated, other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and encoded enzymes, complicating genetic manipulation and in vitro studies of these genes/proteins. The method(s) of the present invention facilitate the rapid discovery of these gene clusters in gene expression libraries.

Of particular interest are cellular "switches" known as receptors which interact with a variety of biomolecules, such as hormones, growth factors, and neurotransmitters, to mediate the transduction of an "external" cellular signaling event into an "internal" cellular signal. External signaling events include the binding of a ligand to the receptor, and internal events include the modulation of a pathway in the cytoplasm or nucleus involved in the growth, metabolism or apoptosis of the cell. Internal events also include the inhibition or activation of transcription of certain nucleic acid sequences, resulting in the increase or decrease in the production or presence of certain molecules (such as nucleic acid, proteins, and/or other molecules affected by this increase or decrease in transcription). Drugs to cure disease or alleviate its symptoms can activate or block any of these events to achieve a desired pharmaceutical effect.

Transduction can be accomplished by a transducing protein in the cell membrane which is activated upon an allosteric change the receptor may undergo upon binding to a specific biomolecule. The "active" transducing protein activates production of so-called "second messenger" molecules within the cell, which then activate certain regulatory proteins within the cell that regulate gene expression or alter some metabolic process. Variations on the theme of this "cascade" of events occur. For example, a receptor may act as its own transducing protein, or a transducing protein may act directly on an intracellular target without mediation by a second messenger.

Signal transduction is a fundamental area of inquiry in biology. For instance, ligand/receptor interactions and the receptor/effector coupling mediated by Guanine nucleotide-binding proteins (G-proteins) are of interest in the study of disease. A large number of G protein-linked receptors funnel extracellular signals as diverse as hormones, growth factors, neurotransmitters, primary sensory stimuli, and other signals through a set of G proteins to a small number of second-messenger systems. The G proteins act as molecular switches with an "on" and "off" state governed by a GTPase cycle. Mutations in G proteins may result in either constitutive activation or loss of expression mutations.

Many receptors convey messages through heterotrimeric G proteins, of which at least 17 distinct forms have been isolated. Additionally, there are several different G protein-dependent effectors. The signals transduced through the heterotrimeric G proteins in mammalian cells influence intracellular events through the action of effector molecules.

Given the variety of functions subserved by G protein-coupled signal transduction, it is not surprising that abnormalities in G protein-coupled pathways can lead to diseases with manifestations as dissimilar as blindness, hormone resistance, precocious puberty and neoplasia. G-protein-coupled receptors are extremely important to drug research efforts. It is estimated that up to 60% of today's prescription drugs work by somehow interacting with G protein-coupled receptors. However, these drugs were developed using classical medicinal chemistry and without a knowledge of the molecular mechanism of action. A more efficient drug discovery program could be deployed by targeting individual receptors and making use of information on gene sequence and biological function to develop effective therapeutics. The present invention allows one to, for example, study molecules which affect the interaction of G proteins with receptors, or of ligands with receptors.

Several groups have reported cells which express mammalian G proteins or subunits thereof, along with mammalian receptors which interact with these molecules. For example, WO92/05244 (Apr. 2, 1992) describes a transformed yeast cell which is incapable of producing a yeast G protein α subunit, but which has been engineered to produce both a mammalian G protein α subunit and a mammalian receptor which interacts with the subunit. The authors found that a modified version of a specific mammalian receptor integrated into the membrane of the cell, as shown by studies of the ability of isolated membranes to interact properly with various known agonists and antagonists of the receptor. Ligand binding resulted in G protein-mediated signal transduction.

Another group has described the functional expression of a mammalian adenylyl cyclase in yeast, and the use of the engineered yeast cells in identifying potential inhibitors or activators of the mammalian adenylyl cyclase (WO 95/30012). Adenylyl cyclase is among the best studied of the effector molecules which function in mammalian cells in response to activated G proteins. "Activators" of adenylyl cyclase cause the enzyme to become more active, elevating the cAMP signal of the yeast cell to a detectable degree.

"Inhibitors" cause the cyclase to become less active, reducing the cAMP signal to a detectable degree. The method describes the use of the engineered yeast cells to screen for drugs which activate or inhibit adenylyl cyclase by their action on G protein-coupled receptors.

When attempting to identify genes encoding bioactivities of interest from complex environmental expression libraries, the rate limiting steps in discovery occur at the both DNA cloning level and at the screening level. Screening of complex environmental libraries which contain, for example, 100's of different organisms requires the analysis of several million clones to cover this genomic diversity. An extremely high-throughput screening method has been developed to handle the enormous numbers of clones present in these libraries.

In traditional flow cytometry, it is common to analyze very large numbers of eukaryotic cells in a short period of time. Newly developed flow cytometers can analyze and sort up to 20,000 cells per second. In a typical flow cytometer, individual particles pass through an illumination zone and appropriate detectors, gated electronically, measure the magnitude of a pulse representing the extent of light scattered. The magnitude of these pulses are sorted electronically into "bins" or "channels", permitting the display of histograms of the number of cells possessing a certain quantitative property versus the channel number (Davey and Kell, 1996). It was recognized early on that the data accruing from flow cytometric measurements could be analyzed (electronically) rapidly enough that electronic cell-sorting procedures could be used to sort cells with desired properties into separate "buckets", a procedure usually known as fluorescence-activated cell sorting (Davey and Kell, 1996).

Fluorescence-activated cell sorting has been primarily used in studies of human and animal cell lines and the control of cell culture processes. Fluorophore labeling of cells and measurement of the fluorescence can give quantitative data about specific target molecules or subcellular components and their distribution in the cell population. Flow cytometry can quantitate virtually any cell-associated property or cell organelle for which there is a fluorescent probe (or natural fluorescence). The parameters which can be measured have previously been of particular interest in animal cell culture.

Flow cytometry has also been used in cloning and selection of variants from existing cell clones. This selection, however, has required stains that diffuse through cells passively, rapidly and irreversibly, with no toxic effects or other influences on metabolic or physiological processes. Since, typically, flow sorting has been used to study animal cell culture performance, physiological state of cells, and the cell cycle, one goal of cell sorting has been to keep the cells viable during and after sorting.

There currently are no reports in the literature of screening and discovery of recombinant enzymes in *E. coli* expression libraries by fluorescence activated cell sorting of single cells. Furthermore there are no reports of recovering DNA encoding bioactivities screened by expression screening in *E. coli* using a FACS machine. The present invention provides these methods to allow the extremely rapid screening of viable or non-viable cells to recover desirable activities and the nucleic acid encoding those activities.

A limited number of papers describing various applications of flow cytometry in the field of microbiology and sorting of fluorescence activated microorganisms have, however, been published (Davey and Kell, 1996). Fluorescence and other forms of staining have been employed for microbial discrimination and identification, and in the analysis of the interaction of drugs and antibiotics with microbial cells. Flow cytometry has been used in aquatic biology, where autofluorescence of photosynthetic pigments are used in the identification of algae or DNA stains are used to quantify and count marine populations (Davey and Kell, 1996). Thus, Diaper and Edwards used flow cytometry to detect viable bacteria after staining with a range of fluorogenic esters including fluorescein diacetate (FDA) derivatives and CemChrome B, a proprietary stain sold commercially for the detection of viable bacteria in suspension (Diaper and Edwards, 1994). Labeled antibodies and oligonucleotide probes have also been used for these purposes.

Papers have also been published describing the application of flow cytometry to the detection of native and recombinant enzymatic activities in eukaryotes. Betz et al. studied native (non-recombinant) lipase production by the eukaryote, *Rhizopus arrhizus* with flow cytometry. They found that spore suspensions of the mold were heterogeneous as judged by light-scattering data obtained with excitation at 633 nm, and they sorted clones of the subpopulations into the wells of microtiter plates. After germination and growth, lipase production was automatically assayed (turbidimetrically) in the microtiter plates, and a representative set of the most active were reisolated, cultured, and assayed conventionally (Betz et al., 1984).

Scrienc et al. have reported a flow cytometric method for detecting cloned-galactosidase activity in the eukaryotic organism, *S. cerevisiae*. The ability of flow cytometry to make measurements on single cells means that individual cells with high levels of expression (e.g., due to gene amplification or higher plasmid copy number) could be detected. In the method reported, a non-fluorescent compound β-naphthol-β-galactopyranoside) is cleaved by β-galactosidase and the liberated naphthol is trapped to form an insoluble fluorescent product. The insolubility of the fluorescent product is of great importance here to prevent its diffusion from the cell. Such diffusion would not only lead to an underestimation of β-galactosidase activity in highly active cells but could also lead to an overestimation of enzyme activity in inactive cells or those with low activity, as they may take up the leaked fluorescent compound, thus reducing the apparent heterogeneity of the population.

One group has described the use of a FACS machine in an assay detecting fusion proteins expressed from a specialized transducing bacteriophage in the prokaryote *Bacillus subtilis* (Chung, et. al., J. of Bacteriology, April 1994, p. 1977–1984; Chung, et. al., Biotechnology and Bioengineering, Vol. 47, pp. 234–242 (1995)). This group monitored the expression of a lacZ gene (encodes β-galactosidase) fused to the sporulation loci in *subtilis* (spo). The technique used to monitor b-galactosidase expression from spo-lacZ fusions in single cells involved taking samples from a sporulating culture, staining them with a commercially available fluorogenic substrate for β-galactosidase called C8-FDG, and quantitatively analyzing fluorescence in single cells by flow cytometry. In this study, the flow cytometer was used as a detector to screen for the presence of the spo gene during the development of the cells. The device was not used to screen and recover positive cells from a gene expression library or nucleic acid for the purpose of discovery.

Another group has utilized flow cytometry to distinguish between the developmental stages of the deltaproteobacteria *Myxococcus xanthus* (F. Russo-Marie, et. al., PNAS, Vol. 90, pp.8194–8198, September 1993). As in the previously described study, this study employed the capabilities of the FACS machine to detect and distinguish genotypically identical cells in different development regulatory states. The screening of an enzymatic activity was used in this study as an indirect measure of developmental changes.

The lacZ gene from *E. coli* is often used as a reporter gene in studies of gene expression regulation, such as those to determine promoter efficiency, the effects of trans-acting factors, and the effects of other regulatory elements in bacterial, yeast, and animal cells. Using a chromogenic substrate, such as ONPG (o-nitrophenyl-(-D-galactopyranoside), one can measure expression of β-galactosidase in cell cultures; but it is not possible to monitor expression in individual cells and to analyze the heterogeneity of expression in cell populations. The use of fluorogenic substrates, however, makes it possible to determine β-galactosidase activity in a large number of individual cells by means of flow cytometry. This type of determination can be more informative with regard to the physiology of the cells, since gene expression can be correlated with the stage in the mitotic cycle or the viability under certain conditions. In 1994, Plovins et al., reported the use of fluorescein-Di-β-D-galactopyranoside (FDG) and $C_{12}$-FDG as substrates for β-galactosidase detection in animal, bacterial, and yeast cells. This study compared the two molecules as substrates for β-galactosidase, and concluded that FDG is a better substrate for β-galactosidase detection by flow cytometry in bacterial cells. The screening performed in this study was for the comparison of the two substrates. The detection capabilities of a FACS machine were employed to perform the study on viable bacterial cells.

Cells with chromogenic or fluorogenic substrates yield colored and fluorescent products, respectively. Previously, it had been thought that the flow cytometry-fluorescence activated cell sorter approaches could be of benefit only for the analysis of cells that contain intracellularly, or are normally physically associated with, the enzymatic activity of small molecule of interest. On this basis, one could only use fluorogenic reagents which could penetrate the cell and which are thus potentially cytotoxic. To avoid clumping of heterogeneous cells, it is desirable in flow cytometry to analyze only individual cells, and this could limit the sensitivity and therefore the concentration of target molecules that can be sensed. Weaver and his colleagues at MIT and others have developed the use of gel microdroplets containing (physically) single cells which can take up nutrients, secret products, and grow to form colonies. The diffusional properties of gel microdroplets may be made such that sufficient extracellular product remains associated with each individual gel microdroplet, so as to permit flow cytometric analysis and cell sorting on the basis of concentration of secreted molecule within each microdroplet. Beads have also been used to isolate mutants growing at different rates, and to analyze antibody secretion by hybridoma cells and the nutrient sensitivity of hybridoma cells. The gel microdroplet method has also been applied to the rapid analysis of mycobacterial growth and its inhibition by antibiotics.

The gel microdroplet technology has had significance in amplifying the signals available in flow cytometric analysis, and in permitting the screening of microbial strains in strain improvement programs for biotechnology. Wittrup et al., (Biotechnolo. Bioeng. (1993) 42:351–356) developed a microencapsulation selection method which allows the rapid and quantitative screening of>$10^6$ yeast cells for enhanced secretion of *Aspergillus awamori* glucoamylase. The method provides a 400-fold single-pass enrichment for high-secretion mutants.

Gel microdroplet or other related technologies can be used in the present invention to localize as well as amplify signals in the high throughput screening of recombinant libraries. Cell viability during the screening is not an issue or concern since nucleic acid can be recovered from the microdroplet.

Different types of encapsulation strategies and compounds or polymers can be used with the present invention. For instance, high temperature agaroses can be employed for making microdroplets stable at high temperatures, allowing stable encapsulation of cells subsequent to heat kill steps utilized to remove all background activities when screening for thermostable bioactivities.

There are several hurdles which must be overcome when attempting to detect and sort *E. coli* expressing recombinant enzymes, and recover encoding nucleic acids. FACS systems have typically been based on eukaryotic separations and have not been refined to accurately sort single *E. coli* cells; the low forward and sideward scatter of small particles like *E. coli*, reduces the ability of accurate sorting; enzyme substrates typically used in automated screening approaches, such as umbelifferyl based substrates, diffuse out of *E. coli* at rates which interfere with quantitation. Further, recovery of very small amounts of DNA from sorted organisms can be problematic. The present invention addresses and overcomes these hurdles and offers a novel screening approach.

SUMMARY OF THE INVENTION

The present invention adapts traditional eukaryotic flow cytometry cell sorting systems to high throughput screening for expression clones in prokaryotes. In the present invention, expression libraries derived from DNA, primarily DNA directly isolated from the environment, are screened very rapidly for bioactivities of interest utilizing fluorescense activated cell sorting. These libraries can contain greater than $10^8$ members and can represent single organisms or can represent the genomes of over 100 different microorganisms, species or subspecies.

Accordingly, in one aspect, the present invention provides a process for identifying clones having a specified activity of interest, which process comprises (i) generating one or more expression libraries derived from nucleic acid directly isolated from the environment; and (ii) screening said libraries utilizing a high throughput cell analyzer, preferably a fluorescence activated cell sorter, to identify said clones.

More particularly, the invention provides a process for identifying clones having a specified activity of interest by (i) generating one or more expression libraries made to contain nucleic acid directly or indirectly isolated from the environment; (ii) exposing said libraries to a particular substrate or substrates of interest; and (iii) screening said exposed libraries utilizing a high throughput cell analyzer, preferably a fluorescence activated cell sorter, to identify clones which react with the substrate or substrates.

In another aspect, the invention also provides a process for identifying clones having a specified activity of interest by (i) generating one or more expression libraries derived from nucleic acid directly or indirectly isolated from the environment; and (ii) screening said exposed libraries utilizing an assay requiring a binding event or the covalent modification of a target, and a high throughput cell analyzer, preferably a fluorescence activated cell sorter, to identify positive clones.

The invention further provides a method of screening for an agent that modulates the activity of a target protein or other cell component (e.g., nucleic acid), wherein the target and a selectable marker are expressed by a recombinant cell, by co-encapsulating the agent in a micro-environment with the recombinant cell expressing the target and detectable marker and detecting the effect of the agent on the activity of the target cell component.

In another embodiment, the invention provides a method for enriching for target DNA sequences containing at least a partial coding region for at least one specified activity in a DNA sample by co-encapsulating a mixture of target DNA obtained from a mixture of organisms with a mixture of DNA probes including a detectable marker and at least a portion of a DNA sequence encoding at least one enzyme having a specified enzyme activity and a detectable marker; incubating the co-encapsulated mixture under such conditions and for such time as to allow hybridization of complementary sequences and screening for the target DNA. Optionally the method further comprises transforming host cells with recovered target DNA to produce an expression library of a plurality of clones.

The invention further provides a method of screening for an agent that modulates the interaction of a first test protein linked to a DNA binding moiety and a second test protein linked to a transcriptional activation moiety by co-encapsulating the agent with the first test protein and second test protein in a suitable microenvironment and determining the ability of the agent to modulate the interaction of the first test protein linked to a DNA binding moiety with the second test protein covalently linked to a transcriptional activation moiety, wherein the agent enhances or inhibits the expression of a detectable protein. Preferably, screening is by FACS analysis.

DETAILED DESCRIPTION OF PREFERRED EMBODIMENTS

Figure 1:
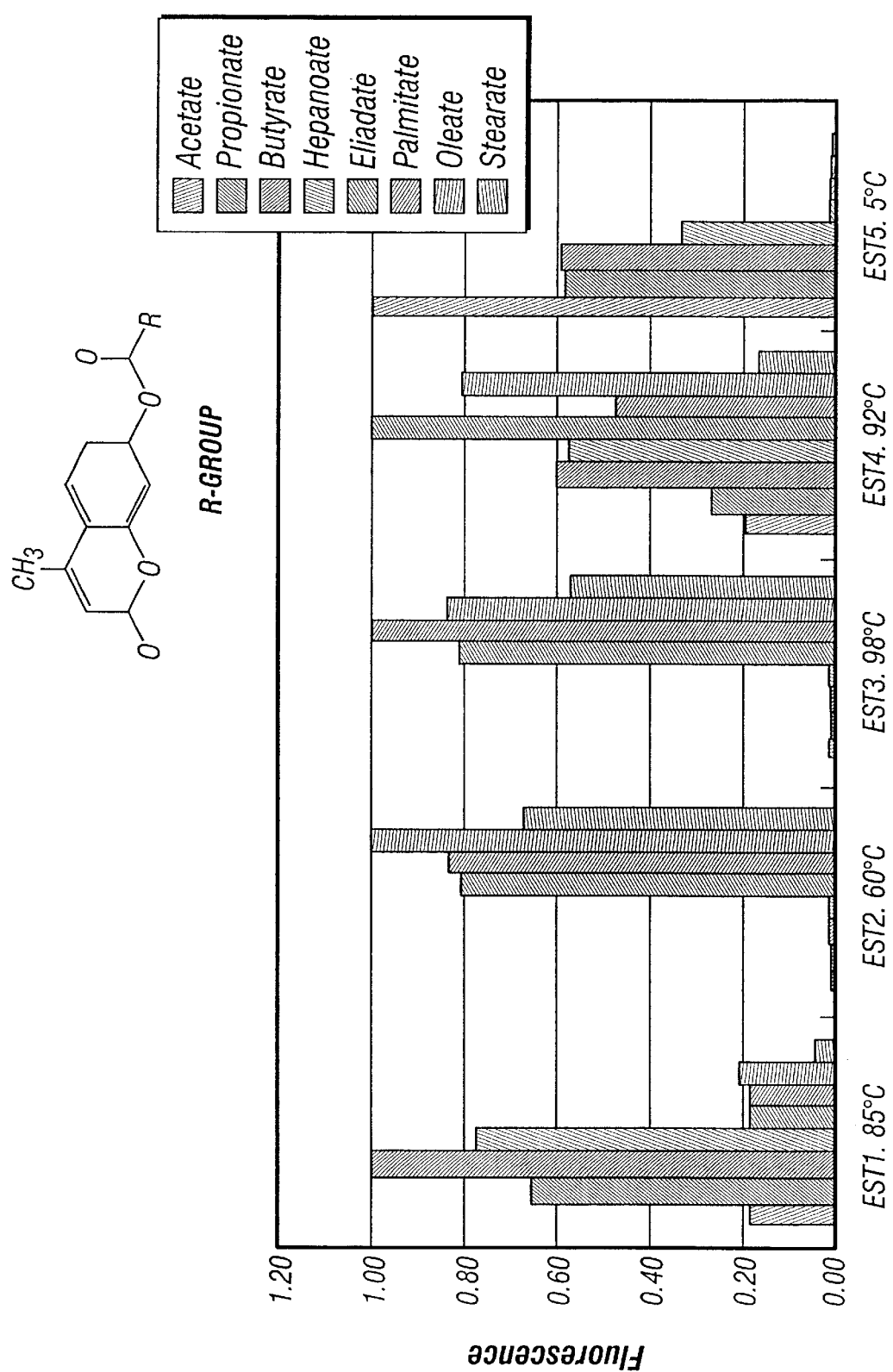
FIG. 1 illustrates the substrate spectrum fingerprints and optimum reaction temperatures of five of novel esterases showing the diversity in these enzymes. EST# indicates the different enzyme; the temperatures indicate the optimal growth temperatures for the organisms from which the esterases were isolated; "E" indicates the relative activity of each esterase enzyme on each of the given substrates indicated (Hepanoate being the reference).
Figure 2:
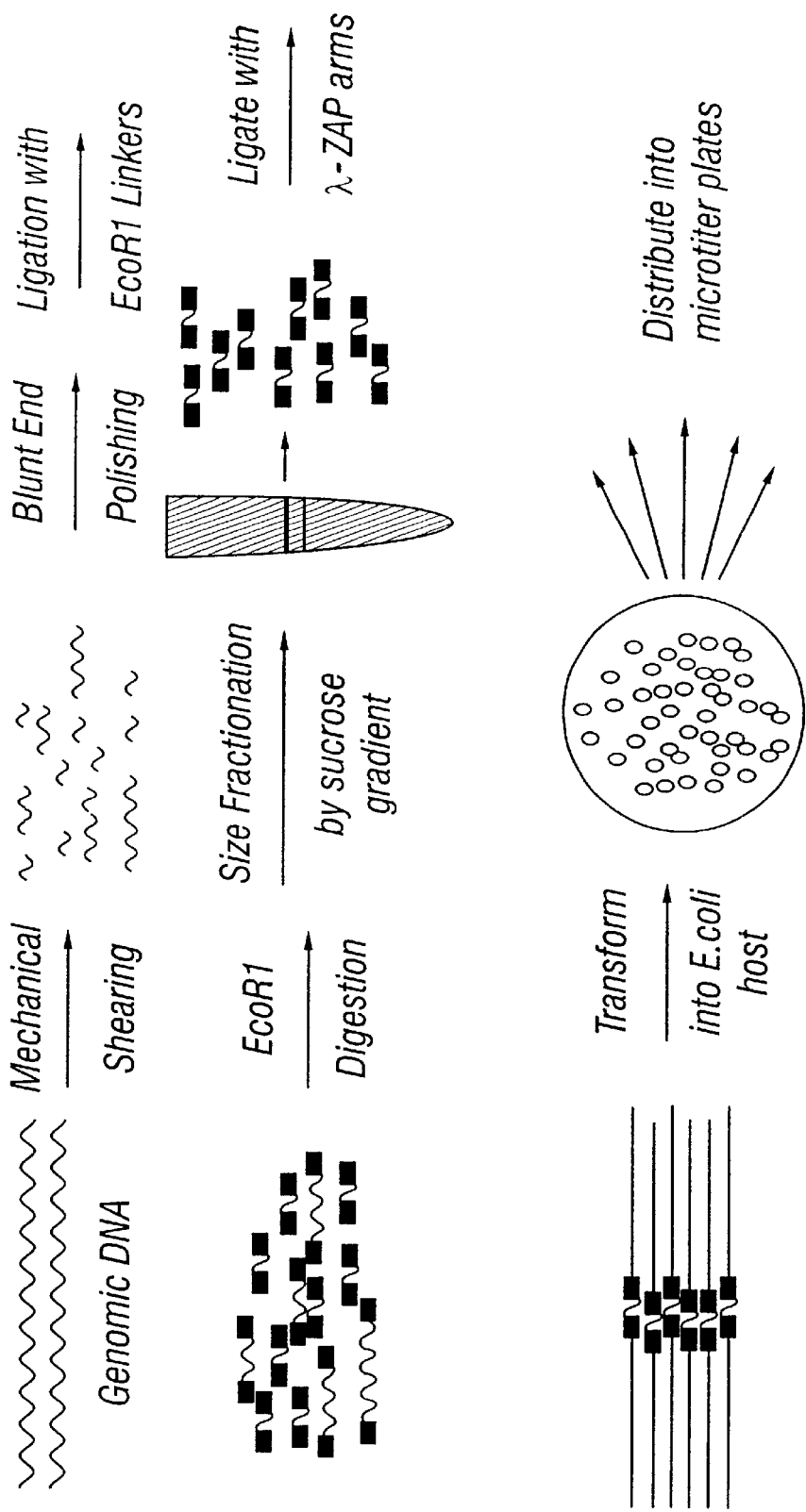
FIG. 2 illustrates the cloning of DNA fragments prepared by random cleavage of target DNA to generate a representative library as described in Example 1.

In the present invention, for example, gene libraries generated from one or more uncultivated microorganisms are screened for an activity of interest. Expression gene libraries are generated, clones are either exposed to the substrate or substrate(s) of interest, hybridized to a probe of interest, or bound to a detectable ligand and positive clones are identified and isolated via fluorescence activated cell sorting. Cells can be viable or non-viable during the process or at the end of the process, as nucleic acid encoding a positive activity can be isolated and cloned utilizing techniques well known in the art.

This invention differs from fluorescense activated cell sorting, as normally performed, in several aspects. Previously, FACS machines have been employed in the studies focused on the analyses of eukaryotic and prokaryotic cell lines and cell culture processes. FACS has also been utilized to monitor production of foreign proteins in both eukaryotes and prokaryotes to study, for example, differential gene expression, etc. The detection and counting capabilities of the FACS system have been applied in these examples. However, FACS has never previously been employed in a discovery process to screen for and recover bioactivities in prokaryotes. Furthermore, the present invention does not require cells to survive, as do previously described technologies, since the desired nucleic acid (recombinant clones) can be obtained from alive or dead cells. The cells only need to be viable long enough to produce the compound to be detected, and can thereafter be either viable or non-viable cells so long as the expressed biomolecule remains active. The present invention also solves problems that would have been associated with detection and sorting of E. coli expressing recombinant enzymes, and recovering encoding nucleic acids. Additionally, the present invention includes within its embodiments any apparatus capable of detecting fluorescent wavelengths associated with biological material, such apparatii are defined herein as fluorescent analyzers (one example of which is a FACS).

The use of a culture-independent approach to directly clone genes encoding novel enzymes from environmental samples allows one to access untapped resources of biodiversity. The approach is based on the construction of "environmental libraries" which represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

In the evaluation of complex environmental expression libraries, a rate limiting step previously occurred at the level of discovery of bioactivities. The present invention allows the rapid screening of complex environmental expression libraries, containing, for example, thousands of different organisms. The analysis of a complex sample of this size requires one to screen several million clones to cover this genomic biodiversity. The invention represents an extremely high-throughput screening method which allows one to assess this enormous number of clones. The method disclosed allows the screening anywhere from about 30 million to about 200 million clones per hour for a desired biological activity. This allows the thorough screening of environmental libraries for clones expressing novel biomolecules.

The present invention combines a culture-independent approach to directly clone genes encoding novel bioactivities from environmental samples with an extremely high throughput screening system designed for the rapid discovery of new biomolecules.

The strategy begins with the construction of gene libraries which represent the genome(s) of microorganisms archived in cloning vectors that can be propagated in E. coli or other suitable prokaryotic hosts. Preferably, "environmental libraries" which represent the collective genomes of naturally occurring microorganisms are generated. In this case, because the cloned DNA is extracted directly from environmental samples, the libraries are not limited to the small fraction of prokaryotes that can be grown in pure culture. In addition, "normalization" can be performed on the environmental nucleic acid as one approach to more equally represent the DNA from all of the species present in the original sample. Normalization techniques can dramatically increase the efficiency of discovery from genomes which may represent minor constituents of the environmental sample. Normalization is preferable since at least one study has demonstrated that an organism of interest can be underrepresented by five orders of magnitude compared to the dominant species.

The method of the present invention begins with the construction of gene libraries which represent the collective genomes of naturally occurring organisms archived in cloning vectors that can be propagated in suitable prokaryotic hosts. The microorganisms from which the libraries may be prepared include prokaryotic microorganisms, such as Eubacteria and Archaebacteria, and lower eukaryotic microorganisms such as fungi, some algae and protozoa. Libraries may be produced from environmental samples in which case DNA may be recovered without culturing of an organism or the DNA may be recovered from a cultured organism is described and exemplified in detail in co-pending, commonly assigned U.S. Ser. No. 08/657,409, filed Jun. 6, 1996, which is incorporated herein by reference. Such microorganisms may be extremophiles, such as hyperthermophiles, psychrophiles, psychrotrophs, halophiles, alkalophiles, acidophiles, etc.

Sources of microorganism DNA as a starting material library from which target DNA is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either a culturable or non-culturable organism and employed to produce an appropriate recombinant expression library for subsequent determination of enzyme or other biological activity. Prokaryotic expression libraries created from such starting material which includes DNA from more than one species are defined herein as multispecific libraries.

In one embodiment, viable or non-viable cells isolated from the environment are, prior to the isolation of nucleic acid for generation of the expression gene library, FACS sorted to separate prokaryotic cells from the sample based on, for instance, DNA or AT/GC content of the cells. Various dyes or stains well known in the art, for example those described in "Practical Flow Cytometry", 1995 Wiley-Liss, Inc., Howard M. Shapiro, M.D., are used to intercalate or associate with nucleic acid of cells, and cells are separated on the FACS based on relative DNA content or AT/GC DNA content in the cells. Other criteria can also be used to separate prokaryotic cells from the sample, as well. DNA is then isolated from the cells and used for the generation of expression gene libraries, which are then screened using the FACS for activities of interest.

Alternatively, the nucleic acid is isolated directly from the environment and is, prior to generation of the gene library, sorted based on DNA or AT/GC content. DNA isolated directly from the environment, is used intact, randomly sheared or digested to general fragmented DNA. The DNA is then bound to an intercalating agent as described above, and separated on the analyzer based on relative base content to isolate DNA of interest. Sorted DNA is then used for the generation of gene libraries, which are then screened using the analyzer for activities of interest.

The present invention can further optimize methods for isolation of activities of interest from a variety of sources, including consortias of microorganisms, primary enrichments, and environmental "uncultivated" samples, to make libraries which have been "normalized" in their representation of the genome populations in the original samples. and to screen these libraries for enzyme and other bioactivities. Libraries with equivalent representation of genomes from microbes that can differ vastly in abundance in natural populations are generated and screened. This "normalization" approach reduces the redundancy of clones from abundant species and increases the representation of clones from rare species. These normalized libraries allow for greater screening efficiency resulting in the identification of cells encoding novel biological catalysts.

One embodiment for forming a normalized library from an environmental sample begins with the isolation of nucleic acid from the sample. This nucleic acid can then be fractionated prior to normalization to increase the chances of cloning DNA from minor species from the pool of organisms sampled. DNA can be fractionated using a density centrifugation technique, such as a cesium-chloride gradient. When an intercalating agent, such as bis-benzimide is employed to change the buoyant density of the nucleic acid, gradients will fractionate the DNA based on relative base content. Nucleic acid from multiple organisms can be separated in this manner, and this technique can be used to fractionate complex mixtures of genomes. This can be of particular value when working with complex environmental samples. Alternatively, the DNA does not have to be fractionated prior to normalization. Samples are recovered from the fractionated DNA, and the strands of nucleic acid are then melted and allowed to selectively reanneal under fixed conditions ($C_o t$ driven hybridization). When a mixture of nucleic acid fragments is melted and allowed to reanneal under stringent conditions, the common sequences find their complementary strands faster than the rare sequences. After an optional single-stranded nucleic acid isolation step, single-stranded nucleic acid representing an enrichment of rare sequences is amplified using techniques well known in the art, such as a polymerase chain reaction (Barnes, 1994), and used to generate gene libraries. This procedure leads to the amplification of rare or low abundance nucleic acid molecules, which are then used to generate a gene library which can be screened for a desired bioactivity. While DNA will be recovered, the identification of the organism(s) originally containing the DNA may be lost. This method offers the ability to recover DNA from "unclonable" sources.

Hence, one embodiment for forming a normalized library from environmental sample(s) is by (a) isolating nucleic acid from the environmental sample(s); (b) optionally fractionating the nucleic acid and recovering desired fractions; and (c) optionally normalizing the representation of the DNA within the population so as to form a normalized expression library from the DNA of the environmental sample(s). The "normalization" process is described and exemplified in detail in co-pending, commonly assigned U.S. Ser. No. 08/665,565, filed Jun. 18, 1996, which is incorporated herein by reference.

The preparation of DNA from the sample is an important step in the generation of normalized or non-normalized DNA libraries from environmental samples composed of uncultivated organisms, or for the generation of libraries from cultivated organisms. DNA can be isolated from samples using various techniques well known in the art (Nucleic Acids in the Environment Methods & Applications, J. T. Trevors, D. D. van Elsas, Springer Laboratory, 1995). Preferably, DNA obtained will be of large size and free of enzyme inhibitors or other contaminants. DNA can be isolated directly from an environmental sample (direct lysis), or cells may be harvested from the sample prior to DNA recovery (cell separation). Direct lysis procedures have several advantages over protocols based on cell separation. The direct lysis technique provides more DNA with a generally higher representation of the microbial community, however, it is sometimes smaller in size and more likely to contain enzyme inhibitors than DNA recovered using the cell separation technique. Very useful direct lysis techniques have been described which provide DNA of high molecular weight and high purity (Barns, 1994; Holben, 1994). If inhibitors are present, there are several protocols which utilize cell isolation which can be employed (Holben, 1994). Additionally, a fractionation technique, such as the bis-benzimide separation (cesium chloride isolation) described, can be used to enhance the purity of the DNA.

Isolation of total genomic DNA from extreme environmental samples varies depending on the source and quantity of material. Uncontaminated, good quality (>20 kbp) DNA is required for the construction of a representative library. A successful general DNA isolation protocol is the standard cetyl-trimethyl-ammonium-bromide (CTAB) precipitation technique. A biomass pellet is lysed and proteins digested by the nonspecific protease, proteinase K, in the presence of the detergent SDS. At elevated temperatures and high salt concentrations, CTAB forms insoluble complexes with denatured protein, polysaccharides and cell debris. Chloroform extractions are performed until the white interface containing the CTAB complexes is reduced substantially. The nucleic acids in the supernatant are precipitated with isopropanol and resuspended in TE buffer.

For cells which are recalcitrant to lysis, a combination of chemical and mechanical methods with cocktails of various cell-lysing enzymes may be employed. Isolated nucleic acid may then further be purified using small cesium gradients.

Gene libraries can be generated by inserting the DNA isolated or derived from a sample into a vector or a plasmid. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmids and methods for introduction and packaging into them are described herein.

The following outlines a general procedure for producing libraries from both culturable and non-culturable organisms: obtain Biomass DNA Isolation (various methods), shear DNA (for example, with a 25 gauge needle), blunt DNA, methylate DNA, ligate to linkers, cut back linkers, size fractionate (for example, use a Sucrose Gradient), ligate to lambda expression vector, package (in vitro lambda packaging extract), plate on *E. coli* host and amplify As detailed in FIG. 1, cloning DNA fragments prepared by random cleavage of the target DNA generates a representative library. DNA dissolved in TE buffer is vigorously passed through a 25 gauge double-hubbed needle until the sheared fragments are in the desired size range. The DNA ends are "polished" or blunted with Mung Bean Nuclease, and EcoRi restriction sites in the target DNA are protected with EcoRI Methylase. EcoRI linkers (GGAATTCC) are ligated to the blunted/protected DNA using a very high molar ratio of linkers to target DNA. This lowers the probability of two DNA molecules ligating together to create a chimeric clone. The linkers are cut back with EcoRi restriction endonuclease and the DNA is size fractionated. The removal of sub-optimal DNA fragments and the small linkers is critical because ligation to the vector will result in recombinant molecules that are unpackageable, or the construction of a library containing only linkers as inserts. Sucrose gradient fractionation is used since it is extremely easy, rapid and reliable. Although the sucrose gradients do not provide the resolution of agarose gel isolations, they do produce DNA that is relatively free of inhibiting contaminants. The prepared target DNA is ligated to the lambda vector, packaged using in vitro packaging extracts and grown on the appropriate *E. coli*.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host.

Another type of vector for use in the present invention contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

The DNA sequence in the expression vector is operatively linked to an appropriate expression control sequence(s) (promoter) to direct RNA synthesis. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), (-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in *E. coli*.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell is a prokaryotic cell, such as a bacterial cell. Particularly preferred host cells are *E. coli*. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). The selection of an appropriate host is deemed to be within the scope of those skilled in the art from the teachings herein.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

It is also contemplated that expression libraries generated can be phage display or cell surface display libraries. Numerous techniques are published in the art for generating such libraries.

After the expression libraries have been generated one can include the additional step of "biopanning" such libraries prior to screening by cell sorting. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) optionally transforming a host with isolated target DNA to produce a library of clones which are screened for the specified biological activity.

The probe DNA used for selectively isolating the target DNA of interest from the DNA derived from at least one microorganism can be a full-length coding region sequence or a partial coding region sequence of DNA for an enzyme of known activity. The original DNA library can be preferably probed using mixtures of probes comprising at least a portion of the DNA sequence encoding an enzyme having the specified enzyme activity. These probes or probe libraries are preferably single-stranded and the microbial DNA which is probed has preferably been converted into single-stranded form. The probes that are particularly suitable are those derived from DNA encoding enzymes having an activity similar or identical to the specified enzyme activity which is to be screened.

The probe DNA should be at least about 10 bases and preferably at least 15 bases. In one embodiment, the entire coding region may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Hybridization techniques for probing a microbial DNA library to isolate target DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Further, it is optional but desirable to perform an amplification of the target DNA that has been isolated. In this embodiment the target DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then screened for clones which display activity for the enzyme of interest.

Having prepared a multiplicity of clones from DNA selectively isolated from an organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened utilizing a FACS machine for such enzyme activity or for a more specific activity. Alternatively, encapsulation techniques such as gel microdroplets, may be employed to localize multiple clones in one location to be screened on a FACS machine for positive expressing clones within the group of clones which can then be broken out into individual clones to be screened again on a FACS machine to identify positive individual clones. Thus, for example, if a clone mixture has hydrolase activity, then the individual clones may be recovered and screened utilizing a FACS machine to determine which of such clones has hydrolase activity. As used herein, "small insert library" means a gene library containing clones with random small size nucleic acid inserts of up to approximately 5000 base pairs. As used herein, "large insert library" means a gene library containing clones with random large size nucleic acid inserts of approximately 5000 up to several hundred thousand base pairs or greater.

As described with respect to one of the above aspects, the invention provides a process for enzyme activity screening of clones containing selected DNA derived from a microorganism which process includes:

screening a library for specified enzyme activity, said library including a plurality of clones, said clones having been prepared by recovering from genomic DNA of a microorganism selected DNA, which DNA is selected by hybridization to at least one DNA sequence which is all or a portion of a DNA sequence encoding an enzyme having the specified activity; and transforming a host with the selected DNA to produce clones which are screened for the specified enzyme activity.

In one embodiment, a DNA library derived from a microorganism is subjected to a selection procedure to select therefrom DNA which hybridizes to one or more probe DNA sequences which is all or a portion of a DNA sequence encoding an enzyme having the specified enzyme activity by:

(a) rendering the double-stranded genomic DNA population into a single-stranded DNA population;

(b) contacting the single-stranded DNA population of (a) with the DNA probe bound to a ligand under conditions permissive of hybridization so as to produce a double-stranded complex of probe and members of the genomic DNA population which hybridize thereto; (c) contacting the double-stranded complex of (b) with a solid phase specific binding partner for said ligand so as to produce a solid phase complex;

(d) separating the solid phase complex from the single-stranded DNA population of (b);

(e) releasing from the probe the members of the genomic population which had bound to the solid phase bound probe;

(f) forming double-stranded DNA from the members of the genomic population of (e);

(g) introducing the double-stranded DNA of (f) into a suitable host to form a library containing a plurality of clones containing the selected DNA; and (h) screening the library for the specified enzyme activity.

In another aspect, the process includes a preselection to recover DNA including signal or secretion sequences. In this manner it is possible to select from the genomic DNA population by hybridization as hereinabove described only DNA which includes a signal or secretion sequence. The following paragraphs describe the protocol for this embodiment of the invention, the nature and function of secretion signal sequences in general and a specific exemplary application of such sequences to an assay or selection process.

A particularly preferred embodiment of this aspect further comprises, after (a) but before (b) above, the steps of:

(a i). contacting the single-stranded DNA population of (a) with a ligand-bound oligonucleotide probe that is complementary to a secretion signal sequence unique to a given class of proteins under conditions permissive of hybridization to form a double-stranded complex;

(a ii). contacting the double-stranded complex of (a i) with a solid phase specific binding partner for said ligand so as to produce a solid phase complex;

(a iii) separating the solid phase complex from the single-stranded DNA population of (a);

(a iv) releasing the members of the genomic population which had bound to said solid phase bound probe; and (a v) separating the solid phase bound probe from the members of the genomic population which had bound thereto.

The DNA which has been selected and isolated to include a signal sequence is then subjected to the selection procedure hereinabove described to select and isolate therefrom DNA which binds to one or more probe DNA sequences derived from DNA encoding an enzyme(s) having the specified enzyme activity.

This procedure is described and exemplified in U.S. Ser. No. 08/692,002, filed Aug. 2, 1996 now U.S. Pat. No. 6,054,267, incorporated herein by reference.

In-vivo biopanning may be performed utilizing a FACS-based machine. Complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

Further, it is possible to combine all the above embodiments such that a normalization step is performed prior to generation of the expression library, the expression library is then generated, the expression library so generated is then biopanned, and the biopanned expression library is then screened using a high throughput cell sorting and screening instrument. Thus there are a variety of options: i.e. (i) one can just generate the library and then screen it; (ii) normalize the target DNA, generate the expression library and screen it; (iii) normalize, generate the library, biopan and screen; or (iv) generate, biopan and screen the library.

The library may, for example, be screened for a specified enzyme activity. For example, the enzyme activity screened for may be one or more of the six IUB classes; oxidoreductases, transferases, hydrolases, lyases, isomerases and ligases. The recombinant enzymes which are determined to be positive for one or more of the IUB classes may then be rescreened for a more specific enzyme activity.

Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e., glycosidases etc.

The clones which are identified as having the specified enzyme activity may then be sequenced to identify the DNA sequence encoding an enzyme having the specified activity. Thus, in accordance with the present invention it is possible to isolate and identify: (i) DNA encoding an enzyme having a specified enzyme activity, (ii) enzymes having such activity (including the amino acid sequence thereof) and (iii) produce recombinant enzymes having such activity.

The present invention may be employed for example, to identify new enzymes having, for example, the following activities which may be employed for the following uses:

Lipase/Esterase

Enantioselective hydrolysis of esters (lipids)/ thioesters, resolution of racemic mixtures, synthesis of optically active acids or alcohols from meso-diesters, selective syntheses, regiospecific hydrolysis of carbohydrate esters, selective hydrolysis of cyclic secondary alcohols, synthesis of optically active esters, lactones, acids, alcohols, transesterification of activated/nonactivated esters, interesterification, optically active lactones from hydroxyesters, egio- and enantioselective ring opening of anhydrides, detergents, fat/oil conversion and cheese ripening.

Protease

Ester/amide synthesis, peptide synthesis, resolution of racemic mixtures of amino acid esters, synthesis of non-natural amino acids and detergents/protein hydrolysis.

Glycosidase/Glycosyl Transferase

Sugar/polymer synthesis, cleavage of glycosidic linkages to form mono, di-and oligosaccharides, synthesis of complex oligosaccharides, glycoside synthesis using UDP-galactosyl transferase, transglycosylation of disaccharides, glycosyl fluorides, aryl galactosides, glycosyl transfer in oligosaccharide synthesis, diastereoselective cleavage of α-glucosylsulfoxides, asymmetric glycosylations, food processing and paper processing.

Phosphatase/Kinase

Synthesis/hydrolysis of phosphate esters, regio- and enantioselective phosphorylation, introduction of phosphate esters, synthesize phospholipid precursors, controlled polynucleotide synthesis, activate biological molecule, selective phosphate bond formation without protecting groups.

Mono/Dioxygenase

Direct oxyfunctionalization of unactivated organic substrates, hydroxylation of alkane, aromatics, steroids, epoxidation of alkenes, enantioselective sulphoxidation, regio- and stereoselective Bayer-Villiger oxidations.

Haloperoxidase

Oxidative addition of halide ion to nucleophilic sites, addition of hypohalous acids to olefinic bonds, ring cleavage of cyclopropanes, activated aromatic substrates converted to ortho and para derivatives 3 diketones converted to 2-halo-derivatives, heteroatom oxidation of sulfur and nitrogen containing substrates, oxidation of enol acetates, alkynes and activated aromatic rings

Lignin Peroxidase/Diarylpropane Peroxidase

Oxidative cleavage of C—C bonds, oxidation of benzylic alcohols to aldehydes, hydroxylation of benzylic carbons, phenol dimerization, hydroxylation of double bonds to form diols, cleavage of lignin aldehydes.

Epoxide Hydrolase

Synthesis of enantiomerically pure bioactive compounds, regio- and enantioselective hydrolysis of epoxide, aromatic and olefinic epoxidation by monooxygenases to form epoxides, resolution of racemic epoxides, hydrolysis of steroid epoxides.

Nitrile Hydratase/Nitrilase

Hydrolysis of aliphatic nitriles to carboxamides, hydrolysis of aromatic, heterocyclic, unsaturated aliphatic nitriles to corresponding acids, hydrolysis of acrylonitrile, production of aromatic and carboxamides, carboxylic acids (nicotinamide, picolinamide, isonicotinamide), regioselective hydrolysis of acrylic dinitrile, amino acids from hydroxynitriles.

Transaminase

Transfer of amino groups into oxo-acids.

Amidase/Acylase

Hydrolysis of amides, amidines, and other C—N bonds, non-natural amino acid resolution and synthesis.

As indicated, the present invention also offers the ability to screen for other types of bioactivities. For instance, the ability to select and combine desired components from a library of polyketides and postpolyketide biosynthesis genes for generation of novel polyketides for study is appealing. The method(s) of the present invention make it possible to and facilitate the cloning of novel polyketide synthases, since one can generate gene banks with clones containing large inserts (especially when using vectors which can accept large inserts, such as the f-factor based vectors), which facilitates cloning of gene clusters.

Preferably, the gene cluster or pathway DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of $E.$ $coli$. As previously indicated, this f-factor of $E.$ $coli$ is a plasmid which affect high-frequency transfer of itself during conjugation and is ideal to achieve and stably propagate large DNA fragments, such as gene clusters from mixed microbial samples. Other examples of vectors include cosmids, bacterial artificial chromosome vectors, and P1 vectors.

Lambda vectors can also accommodate relatively large DNA molecules, have high cloning and packaging efficiencies and are easy to handle and store compared to plasmid vectors. (-ZAP vectors (Stratagene Cloning Systems, Inc.) have a convenient subcloning feature that allows clones in the vector to be excised with helper phage into the pBluescript phagemid, eliminating the time involved in subcloning. The cloning site in these vectors lies downstream of the lac promoter. This feature allows expression of genes whose endogenous promoter does not function in $E.$ $coli$.

The following describes the total number of assays required to test an entire library:

The two main factors which govern the total number of clones that can be pooled and simultaneously screened are (i) the level of gene expression and (ii) enzyme assay sensitivity. As estimate of the level of gene expression is that each $E.$ $coli$ cell infected with lambda will produce $10^3$ copies of the gene product from the insert. FACS instruments are sufficiently sensitive to detect about 500 to 1000 Fluorescein molecules.

Figure 3:
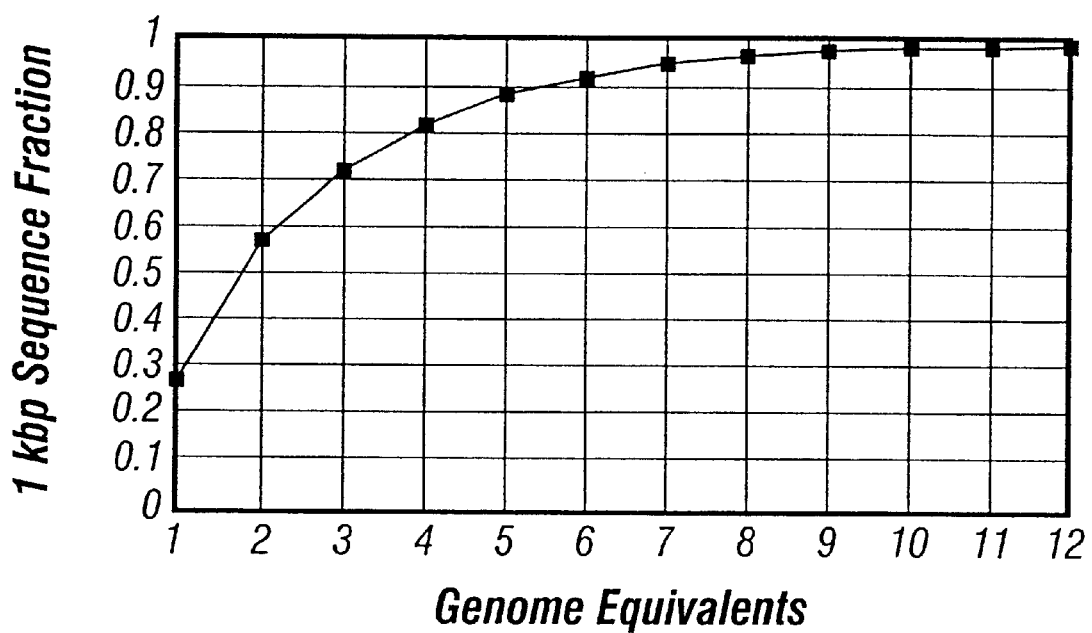
FIG. 3 shows a statistical analysis of the total number of clones to be tested (e.g. the number of genome equivalents). Assuming that mechanical shearing and gradient purification results in normal distribution of DNA fragment sizes with a mean of 4.5 kbp and variance of 1 kbp, the fraction represented of all possible 1 kbp sequences in a 1.8 Mbp genome is plotted in FIG. 3 as a function of increasing genome equivalents.
Figure 4:
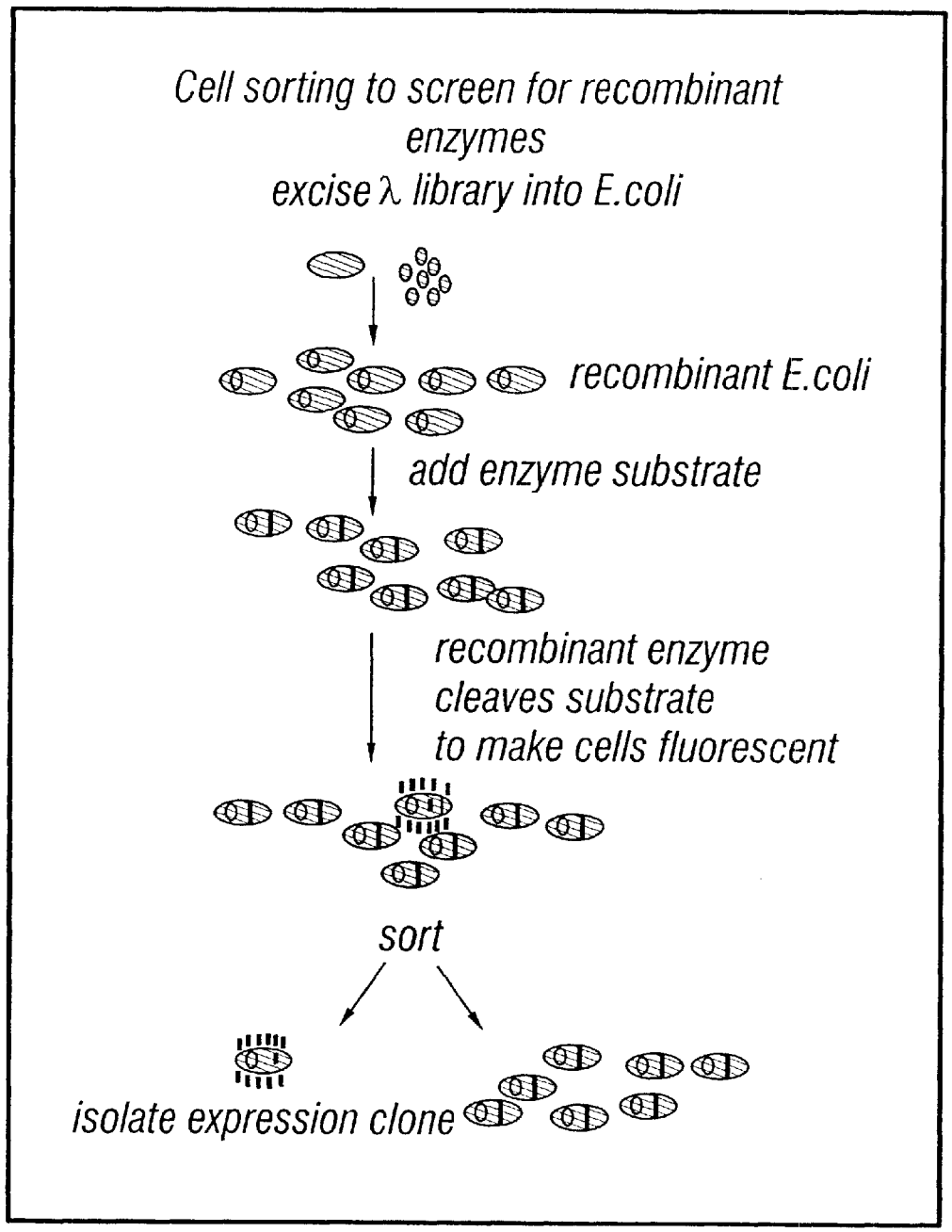
FIG. 4 illustrates the protocol used in the cell sorting method of the invention to screen for recombinant enzymes, in this case using a (library excised into E. coli. The expression clones of interest are isolated by sorting. The procedure is described in detail in Examples 1, 3 and 4.

In order to assess the total number of clones to be tested (e.g., the number of genome equivalents) a statistical analysis was performed. Assuming that mechanical shearing and gradient purification results in a normal distribution of DNA fragment sizes with a mean of 4.5 kbp and variance of 1 kbp, the fraction represented of all possible 1 kbp sequences in a 1.8 Mbp genome is plotted in FIG. 3 as a function of increasing genome equivalents.

Based on these results, approximately 2,000 clones (5 genome equivalents) must be screened to achieve a ~90% probability of obtaining a particular gene. This represents the point of maximal efficiency for library throughput. Assuming that a complex environmental library contains about 1000 different organisms, at least 2,000,000 clones have to be screened to achieve a >90% probability of obtaining a particular gene. This number rises dramatically assuming that the organisms differ vastly in abundance in natural populations.

Substrate can be administered to the cells before or during the process of the cell sorting analysis. In either case a solution of the substrate is made up and the cells are contacted therewith. When done prior to the cell sorting analysis this can be by making a solution which can be administered to the cells while in culture plates or other containers. The concentration ranges for substrate solutions will vary according to the substrate utilized. Commercially available substrates will generally contain instructions on concentration ranges to be utilized for, for instance, cell staining purposes. These ranges may be employed in the determination of an optimal concentration or concentration range to be utilized in the present invention. The substrate solution is maintained in contact with the cells for a period of time and at an appropriate temperature necessary for the substrate to permeablize the cell membrane. Again, this will vary with substrate. Instruments which deliver reagents in stream such as by poppet valves which seal openings in the flow path until activated to permit introduction of reagents (e.g. substrate) into the flow path in which the cells are moving through the analyzer can be employed for substrate delivery.

The substrate is one which is able to enter the cell and maintain its presence within the cell for a period sufficient for analysis to occur. It has generally been observed that introduction of the substrate into the cell across the cell membrane occurs without difficulty. It is also preferable that once the substrate is in the cell it not "leak" back out before reacting with the biomolecule being sought to an extent sufficient to product a detectable response. Retention of the substrate in the cell can be enhanced by a variety of techniques. In one, the substrate compound is structurally modified by addition of a hydrophobic tail. In another certain preferred solvents, such as DMSO or glycerol, can be administered to coat the exterior of the cell. Also the substrate can be administered to the cells at reduced temperature which has been observed to retard leakage of the substrate from the cell's interior.

A broad spectrum of substrates can be used which are chosen based on the type of bioactivity sought. In addition where the bioactivity being sought is in the same class as that of other biomolecules for which a number have known substrates, the bioactivity can be examined using a cocktail of the known substrates for the related biomolecules which are already known. For example, substrates are known for approximately 20 commercially available esterases and the combination of these known substrates can provide detectable, if not optimal, signal production. Substrates are also known and available for glycosidases, proteases, phosphatases, and monoxygenases.

The substrate interacts with the target biomolecule so as to produce a detectable response. Such responses can include chromogenic or fluorogenic responses and the like. The detectable species can be one which results from cleavage of the substrate or a secondary molecule which is so affected by the cleavage or other substrate/biomolecule interaction to undergo a detectable change. Innumerable examples of detectable assay formats are known from the diagnostic arts which use immunoassay, chromogenic assay, and labeled probe methodologies.

Figure 7:
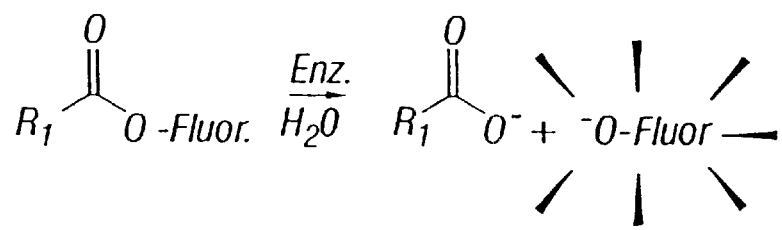
FIG. 7 shows the principle type of fluorescence enzyme assay of deacylation.

Several enzyme assays described in the literature are built around the change in fluorescence which results when the phenolic hydroxyl (or anilino amine) becomes deacylated (or dealkylated) by the action of the enzyme. FIG. 7 shows the basic principle for this type of enzyme assay for deacylation. Any emission or activation of fluorescent wavelengths as a result of any biological process are defined herein as bioactive fluoresence.

In comparison to colorimetric assays, fluorescent based assays are very sensitive, which is a major criteria for single cell assays. There are two main factors which govern the screening of a recombinant enzyme in a single cell: i) the level of gene expression, and ii) enzyme assay sensitivity. To estimate the level of gene expression one can determine how many copies of the gene product will be produced by the host cell given the vector. For instance, one can assume that each E. coli cell infected with pBluescript phagemid (Stratagene Cloning Systems, Inc.) will produce ~$10^3$ copies of the gene product from the insert. The FACS instruments are capable of detecting about 500 to 1,000 fluorescein molecules per cell. Assuming that one enzyme turns over at least one fluorescein based substrate molecule, one cell will display enough fluorescence to be detected by the optics of a fluorescence-activated cell sorter (FACS).

Several methods have been described for using reporter genes to measure gene expression. These reporter genes encode enzymes not ordinarily found in the type of cell being studied, and their unique activity is monitored to determine the degree of transcription. Nolan et al., developed a technique to analyze β-galactosidase expression in mammalian cells employing fluorescein-di-β-D-galactopyranoside (FDG) as a substrate for β-galactosidase, which releases fluorescein, a product that can be detected by a fluorescence-activated cell sorter (FAGS) upon hydrolysis (Nolan et al., 1991). A problem with the use of FDG is that if the assay is performed at room temperature, the fluorescence leaks out of the positively stained cells. A similar problem was encountered in other studies of β-galactosidase measurements in mammalian cells and yeast with FDG as well as other substrates (Nolan et al, 1988; Wittrup et al., 1988). Performing the reaction at 0° C. appreciably decreased the extent of this leakage of fluorescence (Nolan et al., 1988). However this low temperature is not adaptable for screening for, for instance, high temperature -β galactosidases. Other fluorogenic substrates have been developed, such as 5-dodecanoylamino fluorescein di-β-D-galactopyranoside ($C_{12}$-FDG) (Molecular Probes) which differs from FDG in that it is a lipophilic fluorescein derivative that can easily cross most cell membranes under physiological culture conditions. The green fluorescent enzymatic hydrolysis product is retained for hours to days in the membrane of those cells that actively express the lacZ reporter gene. In animal cells $C_{12}$-FDG was a much better substrate, giving a signal which was 100 times higher than the one obtained with FDG (Plovins et al., 1994). However in Gram negative bacteria like E. coli, the outer membrane functions as a barrier for the lipophilic molecule $C_{12}$-FDG and it only passes through this barrier if the cells are dead or damaged (Plovins et al). The fact that $C_{12}$ retains FDG substrate inside the cells indicates that the addition of unpolarized tails may be used for retaining substrate inside the cells with respect to other enzyme substrates.

Figure 8:
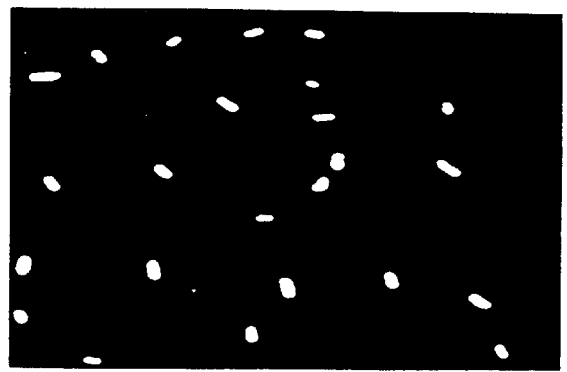
FIG. 8 shows staining of β-galactosidase clones from the hyperthermophilic archaeon Sulfolobus solfataricus expressed in E. coli using $C_{12}$-FDG as enzyme substrate.

The abovementioned β-galactosidase assays may be employed to screen single E. coli cells, expressing recombinant β-D-galactosidase isolated from a hyperthermophilic archaeon such as Sulfolobus solfataricus, on a fluorescent microscope. Cells are cultivated overnight, centrifuged and washed in deionized water and stained with FDG. To increase enzyme activity, cells are heated to 70° C. for 30 minutes and examined with a fluorescence phase contrast microscope. E. coli cell suspensions of the β-galactosidase expressing clone stained with $C_{12}$-FDG show a very bright fluorescence inside single cells (FIG. 8).

The heat treatment of E. coli permeabilizes the cells to allow the substrate to pass through the membrane. Control strains containing plasmid DNA without insert and stained with the same procedure show no fluorescence. Phase contrast microscopy of heated cells reveals that cells maintain their structural integrity up to 2 hours if heated up to 70° C. The lipophilic tail of the modified fluorescein-di-(-D-galactopyranoside prevents leakage of the molecule, even at elevated temperatures. The attachment of a lipophilic carbon chain changes the solubility of substrates tremendously. Thus, substrates containing lipophilic carbon chains can be generated and utilized as screening substrates in the present invention. For instance, the following activities may be detected utilized the indicated substrates. Different methods can be employed for loading substrate inside the cells. Additionally, DMSO can be used as solvent up to a concentration of 50% in water to dissolve and load substrates without significantly dropping the viability of E. coli. Enzyme activity and leakage can be monitored with fluorescence microscopy.

Lipases/Esterases.

Figure 9:
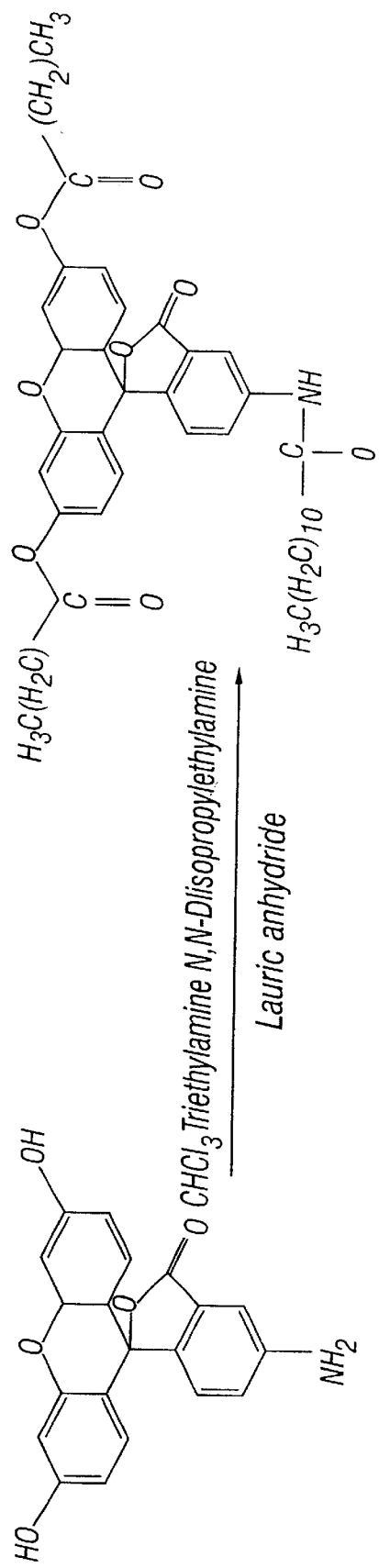
FIG. 9 shows the synthesis of 5-dodecanoyl-aminofluorescein-di-dodecanoic acid.

An acylated derivative of fluorescein can be used to detect esterases such as lipases. The fluorophore is hydrolyzed from the derivative to generate a signal. Acylated derivatives of fluorescein can be synthesized according to FIG. 9. Nine molar equivalents of lauric anhydride triethylamine and N,N-diisopropylethylamine are added to a solution of fluoresceinamine in chloroform. After the reaction is complete, the product 5-dodecanoyl-aminofluorescein-di-dodecanoic acid ($C_{12}$-$FDC_{12}$) is recrystallized.

Proteases.

Figure 10:
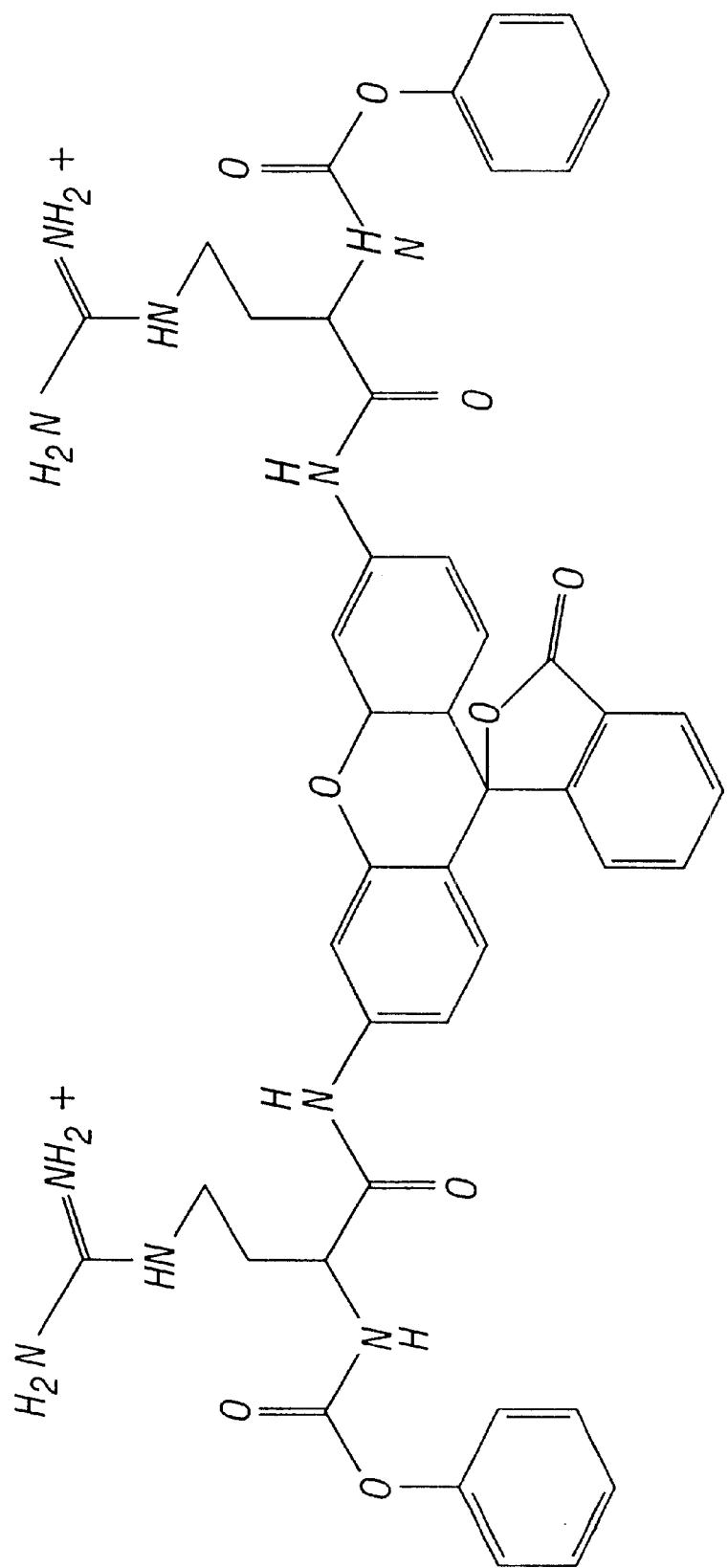
FIG. 10 shows Rhodamine protease substrate.

Proteases can be assayed in the same way as the esterases, with an amide being cleaved instead of an ester. There are now well over 100 different protease substrates available with an acylated fluorophore at the scissile bond. Rhodamine derivatives (FIG. 10), have more lipophilic characteristics compared to fluorescein protease substrates, therefore they make good substrates for more general assays.

Monooxygenases (Dealkylases).

Figure 11:
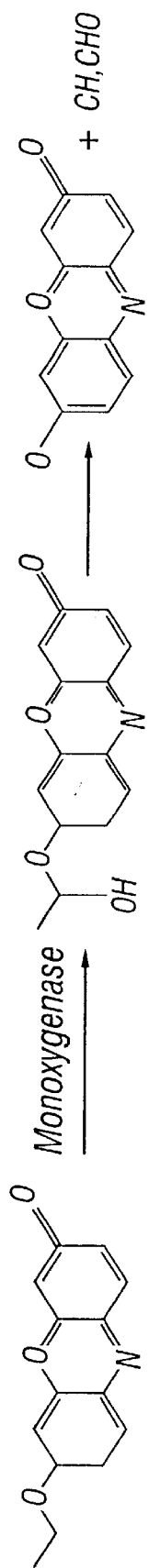
FIG. 11 shows a compound and process that can be used in the detection of monooxygenases.
Figure 12:
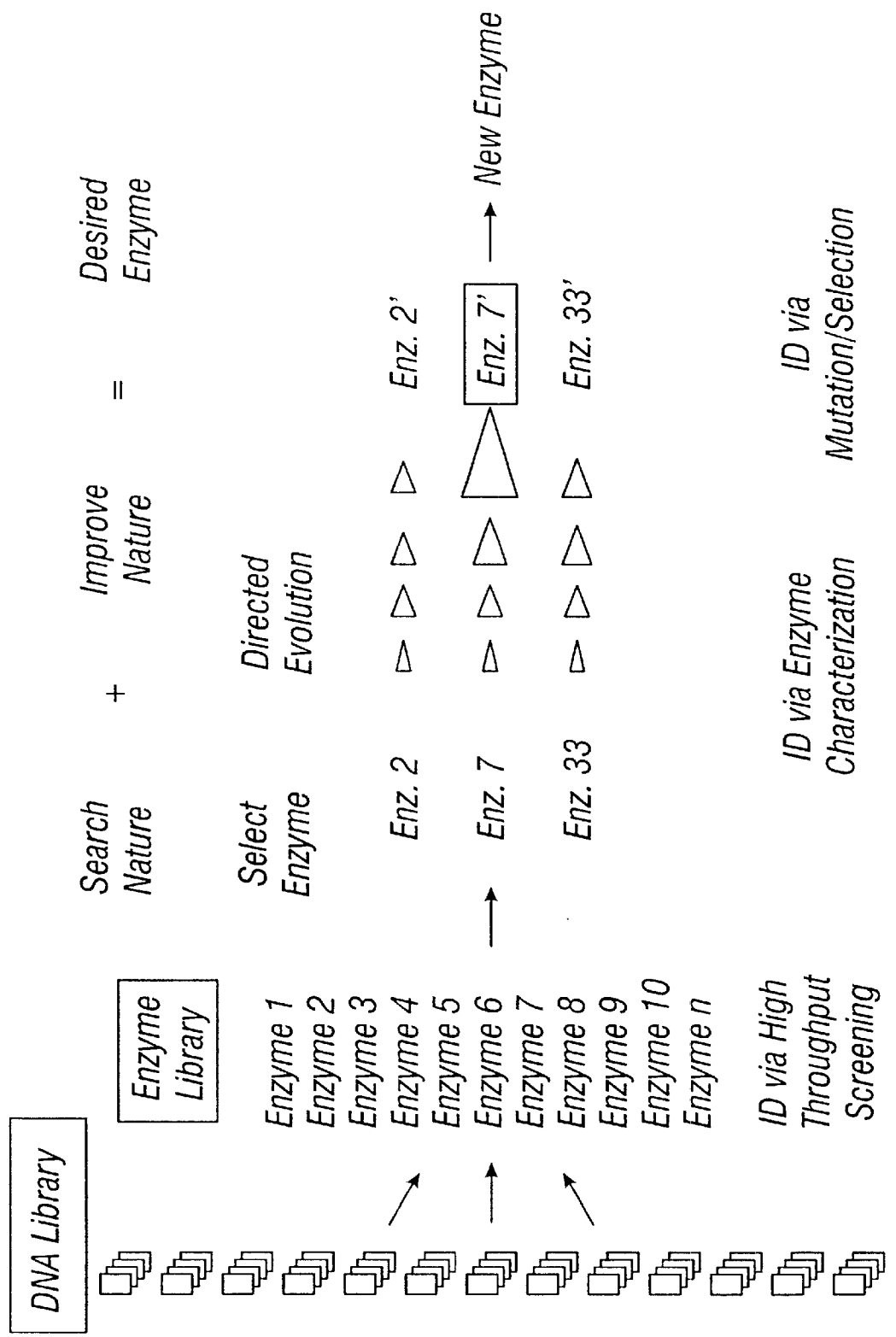
FIG. 12 is a schematic illustration of combinatorial enzyme development using directed evolution.
Figure 13:
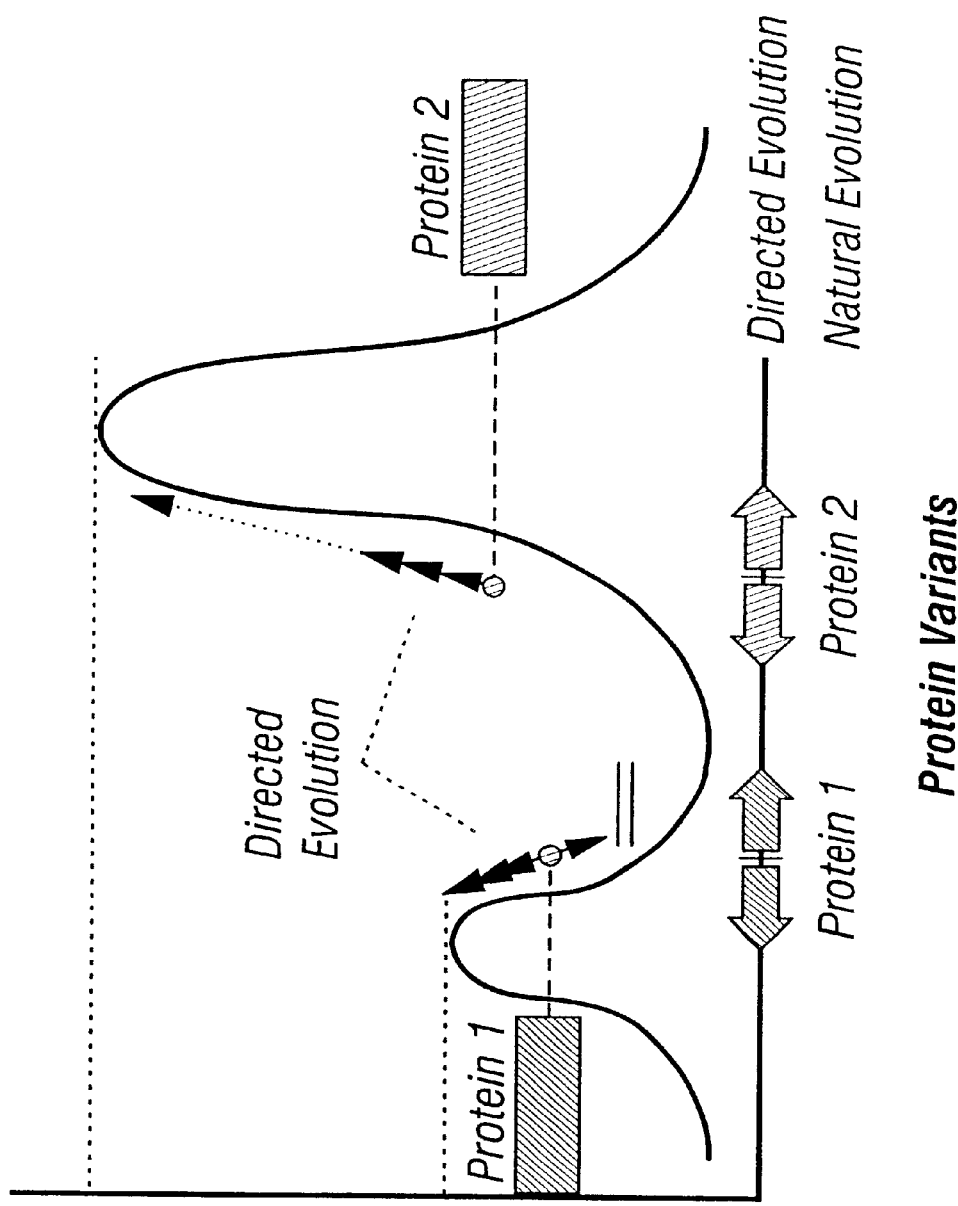
FIG. 13 is a schematic illustration showing bypassing barriers to directed evolution.
Figure 14:
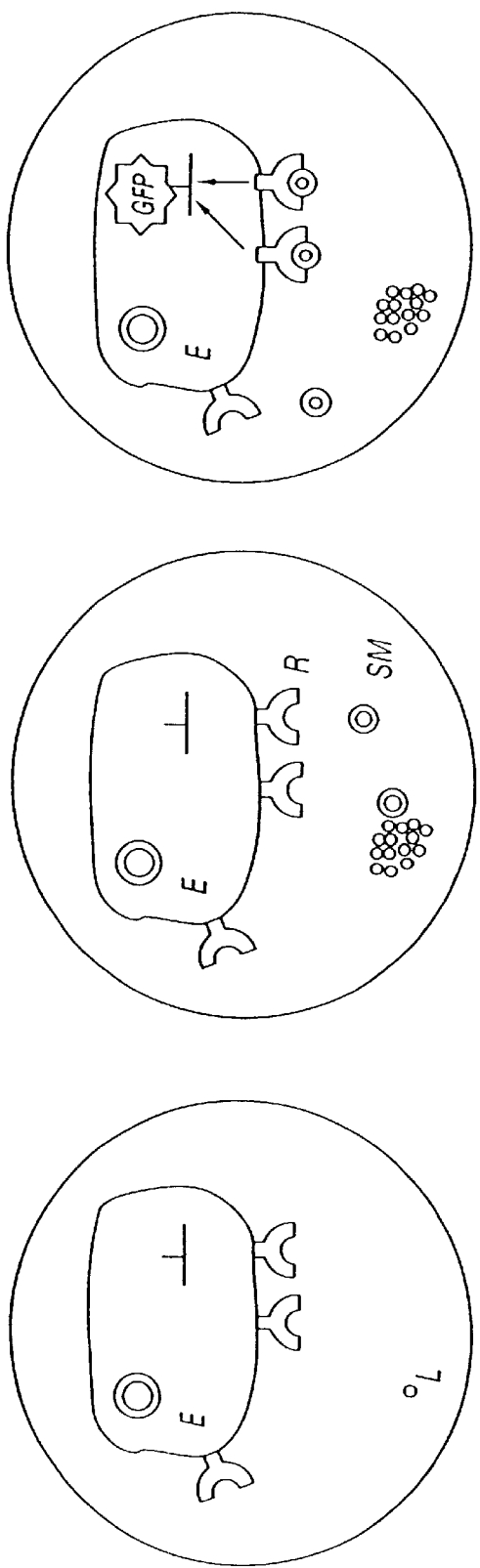
FIG. 14 depicts a co-encapsulation assay for a novel bioactive screen. Cells containing large insert library clones are coencapsulated with a eukaryotic cell containing a receptor. Binding of the receptor by a small molecule expressed from the library ultimately yields expression of a GFP reporter molecule. Encapsulation can occur in a variety of means, including gel microdroplets, liposomes, and ghost cells. Cells are screened via high throughput screening on a fluorescence analyzer.
Figure 15:
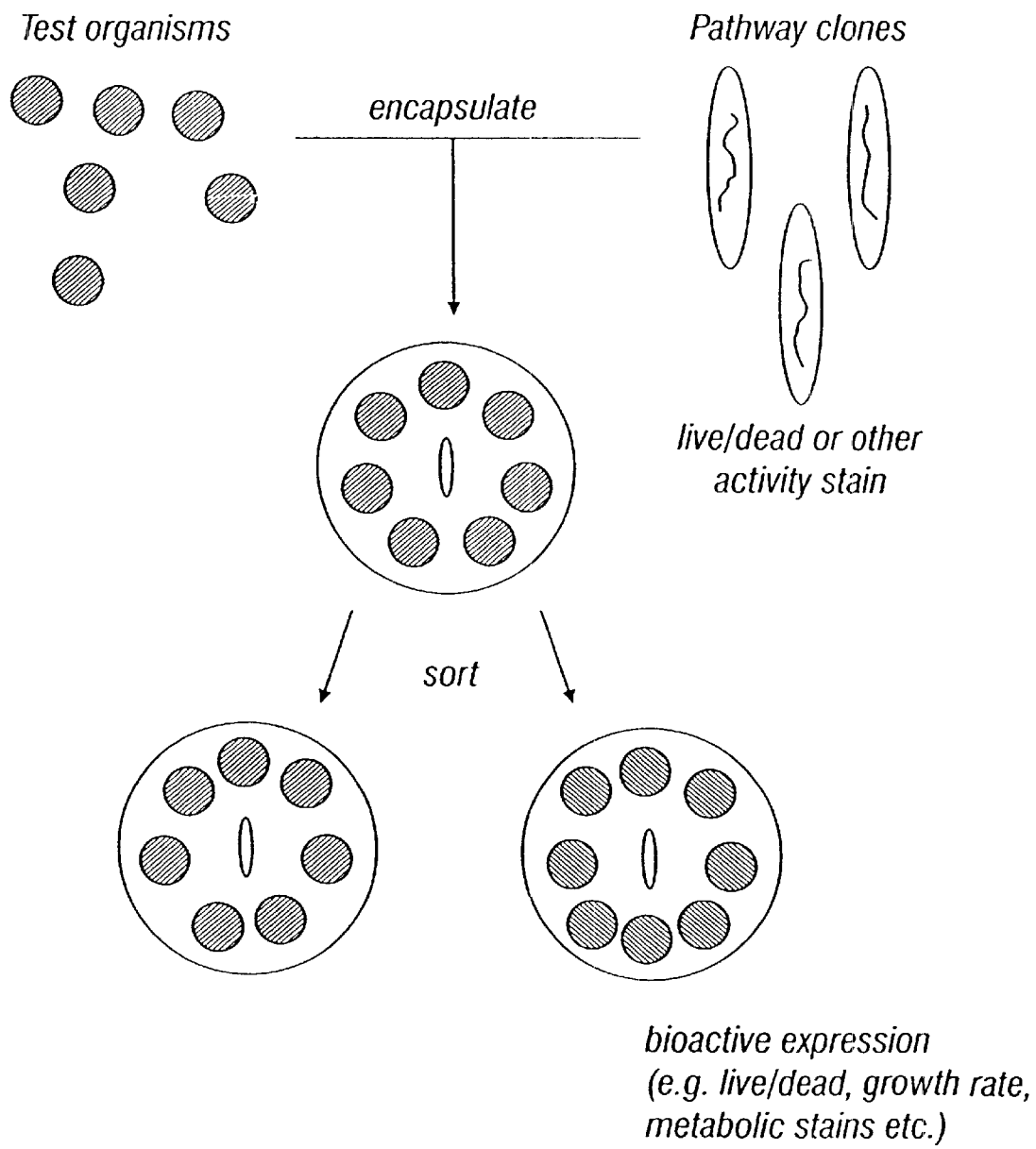
FIG. 15 depicts co-encapsulation of test organisms with pathway clones and sorting based on assays for bioactive expression of clones, such as affects on growth rates of test organisms. In this figure, sorting occurs on a FACS machine.
Figure 16:
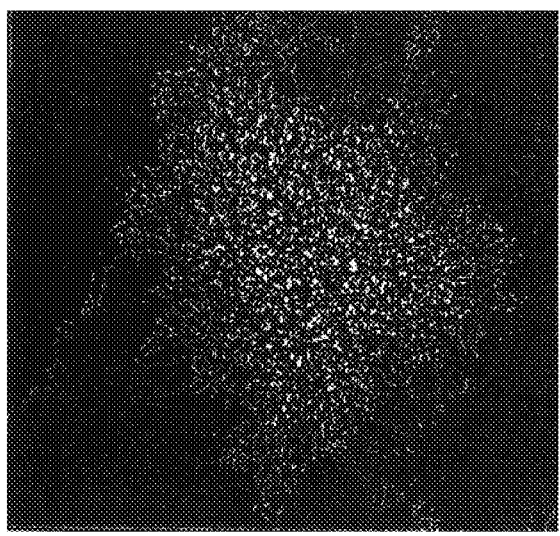
FIG. 16 depicts micrographs of Streptomyces strains. The picture on the left represents Streptomyces lividans mycelia, and the right depicts unicells of another species of Streptomyces which forms unicells (100 × objective phase contrast; taken from an Olympus microscope).
Figure 16:
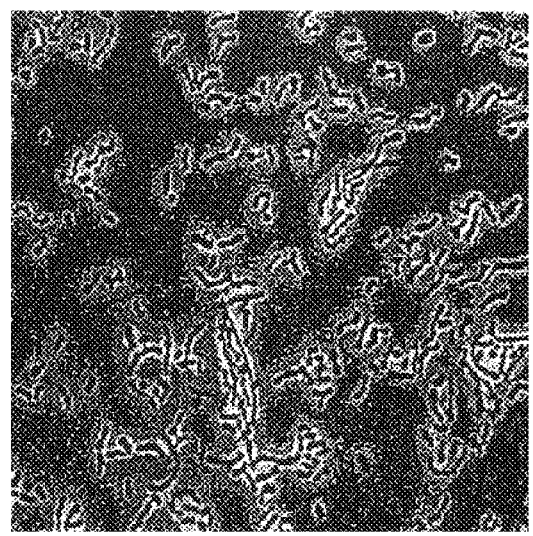
Figure 17:
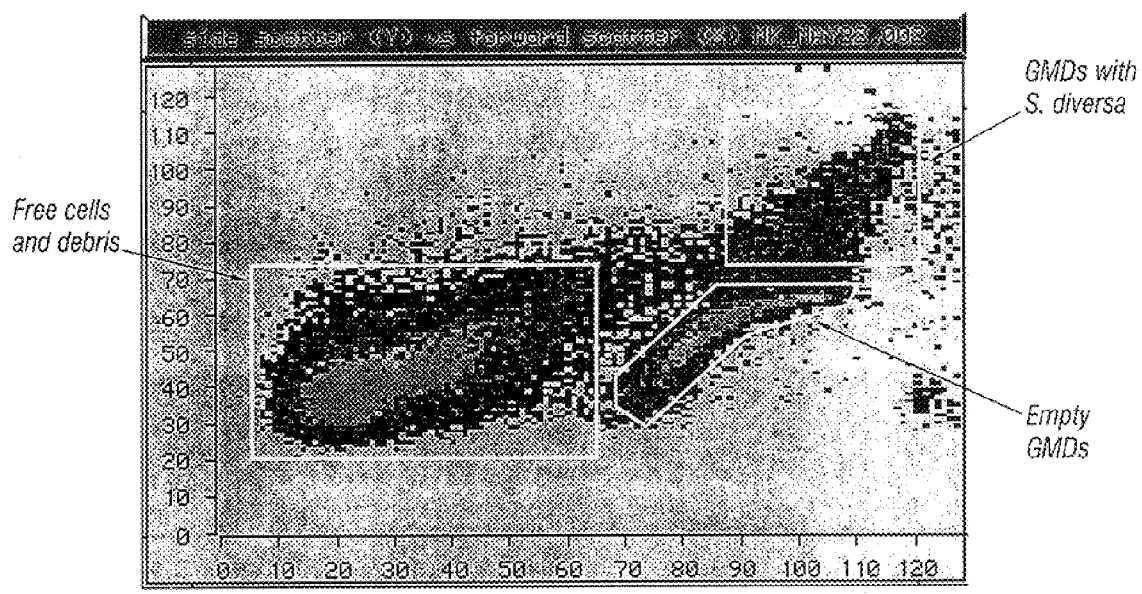
FIG. 17 depicts a side scatter versus forward scatter graph of FACS sorted gel-microdroplets (GMD's) containing a species of Streptomyces which forms unicells. Empty gel-microdroplets are distinguished from free cells and debris, also.
Figure 18:
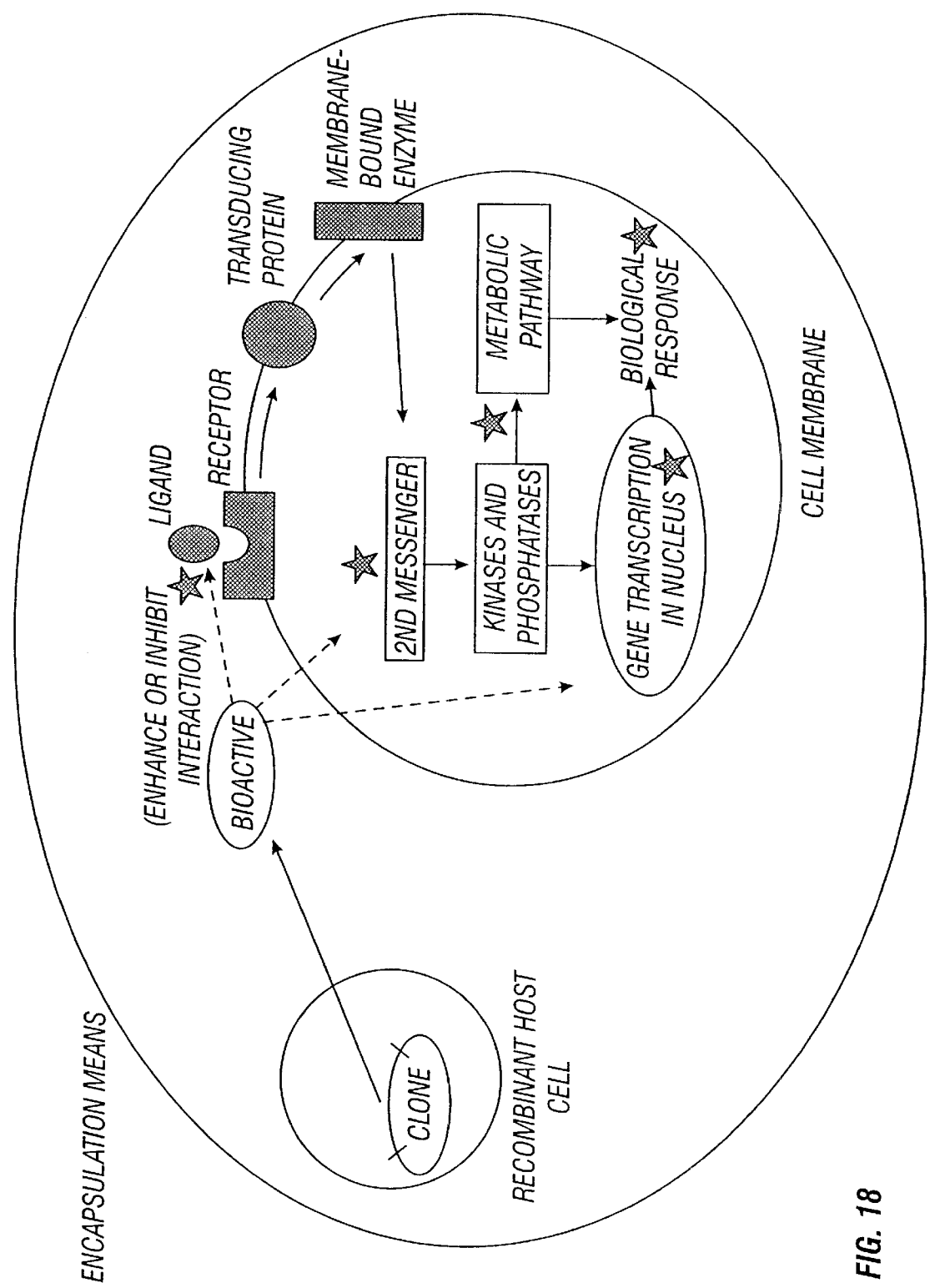
FIG. 18 depicts co-encapsulation of a recombinant host cell containing a clone expressing a small molecule, or agent (labeled Bioactive), with another cell harboring a receptor, transducing protein and other components. Activity of the agent compound on various components of the cell can be assayed. Encapsulation means includes gel microdroplets, liposomes, or ghost cells. The agent can affect ligand/receptor interactions, as depicted, which affect can be assayed via a variety of methods, including detection of increase or decrease in presence of second messenger molecules, detection of transcription or inhibition of transcription of a target gene in the nucleus of the cell (including reporter molecule expression), detection of phosphorylation or kinase of molecules within the cell (all or any of which may be a response to the enhancement or inhibition of the interaction of the ligand with the receptor).

Compounds such as that depicted in FIG. 11 can be used to detected monooxygenases. Hydroxylation of the ethyl group in the compound results in the release of the resorufin fluorophore. Several unmodified coumarin derivatives are also commercially available.

A variety of types of high throughput cell sorting instruments can be used with the present invention. First there is the FACS cell sorting instrument which has the advantage of a very high throughput and individual cell analysis. Other types of instruments which can be used are robotics instruments and time-resolved fluorescence instruments, which can actually measure the fluorescence from a single molecule over an elapsed period of time. Since they are measuring a single molecule, they can simultaneously determine its molecular weight, however their throughput is not as high as the FACS cell sorting instruments.

When screening with the FACS instrument, the trigger parameter is set with logarithmic forward side scatter. The fluorescent signals of positive clones emitted by fluorescein or other fluorescent substrates is distinguished by means of a dichroic mirror and acquired in log mode. For example, "active" clones can be sorted and deposited into microtiter plates. When sorting clones from libraries constructed from single organisms or from small microbial consortia, approximately 50 clones can be sorted into individual microtiter plate wells. When complex environmental mega-libaries (i.e. libraries containing ~$10^8$ clones which represent >100 organisms) about 500 expressing clones should be collected.

Plasmid DNA can then be isolated from the sorted clones using any commercially available automated miniprep machine, such as that from Autogen. The plasmids are then retransformed into suitable expression hosts and assayed for activity utilizing chromogenic agar plate based or automated liquid format assays. Confirmed expression clones can then undergo RFLP analysis to determine unique clones prior to sequencing. The inserts which contain the unique esterase clones can be sequenced, open reading frames (ORF's) identified and the genes PCR subcloned for overexpression. Alternatively, expressing clones can be "bulk sorted" into single tubes and the plasmid inserts recovered as amplified products, which are then subcloned and transformed into suitable vector-hosts systems for rescreening.

Encapsulation techniques may be employed to localize signal, even in cases where cells are no longer viable. Gel microdrops (GMDs) are small (25 to 50 um in diameter) particles made with a biocompatible matrix. In cases of viable cells, these microdrops serve as miniaturized petri dishes because cell progeny are retained next to each other, allowing isolation of cells based on clonal growth. The basic method has a significant degree of automation and high throughput; after the colony size signal boundaries are established, about $10^6$ GMDs per hour can be automatically processed. Cells are encapsulated together with substrates and particles containing a positive clones are sorted. Fluorescent substrate labeled glass beads can also be loaded inside the GMDs. In cases of non-viable cells, GMDs can be employed to ensure localization of signal.

After viable or non-viable cells, each containing a different expression clone from the gene library are screened on a FACS machine, and positive clones are recovered, DNA is isolated from positive clones. The DNA can then be amplified either in vivo or in vitro by utilizing any of the various amplification techniques known in the art. In vivo amplification would include transformation of the clone(s) or subclone(s) of the clones into a viable host, followed by growth of the host. In vitro amplification can be performed using techniques such as the polymerase chain reaction.

Clones found to have the bioactivity for which the screen was performed can also be subjected to directed mutagenesis to develop new bioactivities with desired properties or to develop modified bioactivities with particularly desired properties that are absent or less pronounced in the wild-type enzyme, such as stability to heat or organic solvents. Any of the known techniques for directed mutagenesis are applicable to the invention. For example, particularly preferred mutagenesis techniques for use in accordance with the invention include those described below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" (also known as "DNA shuffling") refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propogation of the DNA in a strain of *E. coli* that carries mutations in one or more of the DNA repair pathways. These "mutator" strains have a higher random mutation rate than that of a wild-type parent. Propogating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993).

All of the references mentioned above are hereby incorporated by reference in their entirety. Each of these techniques is described in detail in the references mentioned.

DNA can be mutagenized, or "evolved", utilizing any one or more of these techniques, and rescreened on the FACS machine to identify more desirable clones. "Fluorescence screening" as utilized herein means screening for any activity of interest utilizing any fluorescent analyzer that detects fluorescence. Internal control reference genes which either express fluorescing molecules, such as those encoding green fluorescent protein, or encode proteins that can turnover fluorescing molecules, such as beta-galactosidase, can be utilized. These internal controls should optimally fluoresce at a wavelength which is different from the wavelength at which the molecule used to detect the evolved molecule(s) emits. DNA is evolved, recloned in a vector which co-expresses these proteins or molecules, transformed into an appropriate host organism, and rescreened utilizing the FACS machine to identify more desirable clones.

An important aspect of the invention is that cells are being analyzed individually. However other embodiments are contemplated which involve pooling of cells and multiple passage screen. This provides for a tiered analysis of biological activity from more general categories of activity, i.e. categories of enzymes, to specific activities of principle interest such as enzymes of that category which are specific to particular substrate molecules.

Members of these libraries can be encapsulated in gel microdroplets, exposed to substrates of interest, such as transition state analogs, and screened based on binding via FACS sorting for activities of interest.

It is anticipated with the present invention that one could employ mixtures of substrates to simultaneously detect multiple activities of interest simultaneously or sequentially. FACS instruments can detect molecules that fluoresce at different wavelengths, hence substrates which fluoresce at different wavelengths and indicate different activities can be employed.

The fluorescence activated cell sorting screening method of the present invention allows one to assay several million clones per hour for a desired bioactivity. This technique provides an extremely high throughput screening process necessary for the screening of extreme biodiverse environmental libraries.

In a preferred embodiment, the present invention provides a novel method for screening for activities, defined as "agents" herein, which affect the action of transducing proteins, such as, for example, G-proteins. In the present invention, cells containing functional transducing proteins (such as membrane bound G-proteins), defined herein as "target cells" or "target(s)", are co-encapsulated with potential agent molecules and screened for affects agent molecules may have on their actions. Potential agent molecules are originally derived from a gene library generated from environmental or other samples, as described herein.

In particular, agents are molecules encoded by a pathway or gene cluster, or molecules generated by the expression of said pathways or clusters. Cells containing nucleic acid expressing the agent, or cells containing nucleic acid expressing activities which act within the cell to yield agent molecules can be utilized for screening. Alternatively, agent molecules can be expressed or generated prior to screening, and subsequently utilized. Cells expressing agent molecules, or agent molecules are coencapsulated, and screened utilizing various methods, such as those described herein.

Agent molecules can exist in or be introduced into the encapsulation particle by various means. Cells expressing genes encoding proteins which act to generate agent molecules (small molecules, for example) can be introduced into encapsulation particles using, for instance, Examples provided herein. Said cells can be prokaryotic or eukaryotic cells. Prokaryotic cells can be bacteria, such as *E. coli*. As previously indicated, genes can alternatively be expressed outside the encapsulation particle, the expression product or molecules generated via action of expressed products (such as small molecules or agent molecules) can be purified from the host, and said agents may be introduced into the encapsulation particle with the functional transducing protein(s), also using the methods described in the Examples below.

Encapsulation can be in beads, high temperature agaroses, gel microdroplets, cells, such as ghost red blood cells or macrophages, liposomes, or any other means of encapsulating and localizing molecules.

For example, methods of preparing liposomes have been described (i.e., U.S. Pat. Nos. 5,653,996, 5,393,530 and 5,651,981), as well as the use of liposomes to encapsulate a variety of molecules U.S. Pat. Nos. 5,595,756, 5,605,703, 5,627,159, 5,652,225, 5,567,433, 4,235,871, 5,227,170). Entrapment of proteins, viruses, bacteria and DNA in erythrocytes during endocytosis has been described, as well (Journal of Applied Biochemistry 4, 418–435 (1982)). Erythrocytes employed as carriers in vitro or in vivo for substances entrapped during hypo-osmotic lysis or dielectric breakdown of the membrane have also been described (reviewed in Ihler, G. M. (1983) J. Pharm. Ther). These techniques are useful in the present invention to encapsulate samples for screening.

"Microenvironment", as used herein, is any molecular structure which provides an appropriate environment for facilitating the interactions necessary for the method of the invention. An environment suitable for facilitating molecular interactions include, for example, liposomes. Liposomes can be prepared from a variety of lipids including phospholipids, glycolipids, steroids, long-chain alkyl esters; e.g., alkyl phosphates, fatty acid esters; e.g., lecithin, fatty amines and the like. A mixture of fatty material may be employed such a combination of neutral steroid, a charge amphiphile and a phospholipid. Illustrative examples of phospholipids include lecithin, sphingomyelin and dipalmitoylphos-phatidylcholine. Representative steroids include cholesterol, cholestanol and lanosterol. Representative charged amphiphilic compounds generally contain from 12–30 carbon atoms. Mono- or dialkyl phosphate esters, or alkyl amines; e.g., dicetyl phosphate, stearyl amine, hexadecyl amine, dilauryl phosphate, and the like.

In addition, agents which potentially enhance or inhibit ligand/receptor interactions may be screened and identified. Thus, the present invention thus provides a method to screen recombinants producing drugs which block or enhance interactions of molecules, such as protein—protein interactions. When screening for compounds which affect G-protein interactions, host cells expressing recombinant clones to be screened are co-encapsulated with membrane bound G-proteins and ligands. Compounds (such as small molecules) diffuse out of host cells, and enhancement or inhibition of G-protein interactions can be evaluated via a variety of methods. Any screening method which allows one to detect an increase or decrease in activity or presence of an intracellular compound or molecule, including nucleic acids and proteins, which results from enhancement or inhibition of ligand/receptor interactions, transducers, such as G-protein interactions, or cascade events occurring inside a cell are useful in the present invention.

For example, the adenylyl cyclase method described above can be utilized in the present invention. Other assays which detect effects, or changes, modulated by effectors are useful in the present invention. The change, or signal, must be detectable against the background, or basal activity of the effector in the absence of the potential small molecule or drug. The signal may be a change in the growth rate of the cells, or other phenotypic changes, such as a color change or luminescence. Production of functional gene products may be impacted by the effect, as well. For example, the production of a functional gene product which is normally regulated by downstream or direct effects created by the transducer or effector can be altered and detected. Said functional genes may include reporter molecules, such as green fluorescent protein, or red fluorescent protein (Biosci Biotechnol Biochem 1995 Oct.; 59(10):1817–1824), or other detectable molecules. These "functional genes" are used as marker genes. "Marker genes" are engineered into the host cell where desired. Modifications to their expression levels causes a phenotypic or other change which is screenable or selectable. If the change is selectable, a phenotypic change creates a difference in the growth or survival rate between cells which express the marker gene and those which do not, or a detectable modification in expression levels of reporter molecules within or around cells. If the change is screenable, the phenotype change creates a difference in some detectable characteristic of the cells, by which the cells which express the marker may be distinguished from those which do not. Selection is preferable to screening.

Rapid assays which measure direct readouts of transcriptional activity are useful in the present invention. For example, placing the bacterial gene encoding lacZ under the control of the FUS1 promoter, activation of the yeast pheromone response pathway can be detected in less than an hour by monitoring the ability of permeabilized yeast to produce color from a chromogenic substrate. Activation of other response pathways may be assayed via similar strategies. Genes encoding detectable molecules, or which create a detectable signal via modification of another molecules, can be utilized to analyze activation or suppression of a response.

The use of fluorescent proteins and/or fluorescent groups and quenching groups in close proximity to one another to assay the presence of enzymes or nucleic acid sequences has been reported (WO 97/28261 and WO 95/13399). In the first of these reactions, fluorescent proteins having the proper emission and excitation spectra are put in physically close proximity to exhibit fluorescence energy transfer. Substrates for enzyme activities are placed between the two proteins, such that cleavage of the substrate by the presence of the enzymatic activity separates the proteins enough to change the emission spectra. Another group utilizes a fluorescent protein and a quencher molecule in close proximity to exhibit "collisional quenching" properties whereby the fluorescence of the fluorescent protein is diminished simply via the proximity of the quenching group. Probe nucleic acid sequences are engineered between the two groups, and a hybridization event between the probe sequence and a target in a sample separates the protein from the quencher enough to yield a fluorescent signal. Still another group has reported a combination of the above strategies, engineering a molecule which utilizes an enzyme substrate flanked by a fluorescent protein on one end and a quencher on the other (EP 0 428 000). It is recognized that these types assays can be employed in the method of the present invention to detect modifications in nucleic acid production (transcriptional activation or repression) and/or enzyme or other protein production (translational modifications) which results from inhibition of or improved association of interacting molecules, such as ligands and receptors, or which results from actions of bioactive compounds directly on transcription of particular molecules.

Fluorescent proteins encoded by genes which can be used to transform host cells and employed in a screen to identify compounds of interest are particularly useful in the present invention. Substrates are localized into the encapsulation means by a variety of methods, including but not limited to the method described herein in the Example below. Cells can also be engineered to contain genes encoding fluorescing molecules. For example, transcriptionally regulated genes can be linked to reporter molecule genes to allow expression (or lack of expression) of the reporter molecule to facilitate detection of the expression of the transcriptionally regulated gene. For example, if the ultimate effect of an agonist or antagonist interacting to enhance or inhibit the binding of a ligand to a receptor, or to enhance or inhibit the effects of any molecule in a pathway, is transcriptional activation or repression of a gene of interest the cell, it is useful to be able to link the activated gene to a reporter gene to facilitate detection of the expression.

Cells can be engineered in variety of ways to allow the assay of the effect of compounds on cellular "events". An "event", as utilized herein, means any cellular function which is modified or event which occurs in response to exposure of the cell, or components of the cell, to molecules expressed by, or ultimately yielded by the expression of, members of gene libraries derived from samples and generated according to the methods described herein. For example, cellular events which can be detected with commercially available products include changes in transmembrane pH (i.e., BCECF pH indicator sold by BioRad Laboratories, Inc., Hercules, Calif.), cell cycle events, such as cell proliferation, cytotoxicity and cell death (i.e., propidium iodide, 5-bromo-2'-deoxy-uridine (BrdU), Annexin-V-FLUOS, and TUNEL (method) sold by Boehringer- Mannheim Research Biochemicals), or production of proteins, such as enzymes. In many instances, the cascade of events begun by membrane protein interactions with other molecules involves modifications, such as phosphorylation or dephosphorylation, of molecules within the cell. Molecules, such as fluorescent substrates, which facilitate detection of these events are useful in the present invention to screen libraries expressing activities of interest. ELISA or colorimetric assays can also be adapted to single cell screening to be utilized to screen libraries according to the present invention.

Probe nucleic acid sequences designed according to the method described above can also be utilized in the present invention to "enrich" a population for desirable clones. "Enrich", as utilized herein, means reducing the number and/or complexity of an original population of molecules. For example, probes are designed to identify specific polyketide sequences, and utilized to enrich for clones encoding polyketide pathways. Fosmid libraries are generated in *E. coli* according to the methods described in the Example herein. Clones are encapsulated and grown to yield encapsulated clonal populations. Cells are lysed and neutralized, and exposed to the probe of interest. Hybridization yields a positive fluorescent signal which can be sorted on a fluorescent cell sorter. Positives can be further screened via expression, or activity, screening. Thus, this aspect of the present invention facilitates the reduction of the complexity of the original population to enrich for desirable pathway clones. These clones can then be utilized for further downstream screening. For example, these clones can be expressed to yield backbone structures (defined herein), which can then be decorated in metabolically rich hosts, and finally screened for an activity of interest. Alternatively, clones can be expressed to yield small molecules directly, which can be screened for an activity of interest. Furthermore, multiple probes can be designed and utilized to allow "multiplex" screening and/or enrichment. "Multiplex" screening and/or enrichment as used herein means that one is screening and/or enriching for more than desirable outcome, simultaneously.

Detectable molecules may be added as substrates to be utilized in screening assays, or genes encoding detectable molecules may be utilized in the method of the present invention.

The present invention provides for strategies to utilize high throughput screening mechanisms described herein to allow for the enrichment for desirable activities from a population of molecules. In one aspect of the present invention, cells are screened for the presence of ubiquitous molecules, such as thioesterase activities, to allow one to enrich for cells producing desirable bioactivities, such as those encoded by polyketide pathways. A variety of screening mechanisms can be employed. For example, identifying and recovering cells possessing thioesterase activities allows one to enrich for cells potentially containing polyketide activities. For example, for aromatic polyketides, the polyketide synthase consists of a single set of enzyme activities, housed either in a single polypeptide chain (type 1) or on separate polypeptides (type II), that act in every cycle. In contrast, complex polyketides are synthesized on multifunctional PKSs that contain a distinct active site for every catalyzed step in chain synthesis. Type I polyketide scaffolds are generated and cleaved from the acyl carrier protein in a final action by a thioesterase-cylcase activity (thioester bond cleaved). One group has even demonstrated that moving the location of the thioester bond along a polyketide pathway clone dictates where the polyketide scaffold will be clipped from the carrier protein (Cortes J., et. al., Science, Vol. 258, 9 June 1995). Hybridization (homology) screening can be employed to identify cells containing thioesterase activities. If hybridization screening is utilized, sequences (partial or complete) of genes encoding known thioesterases can be utilized as identifying probes. Alternatively, probes containing probing sequences derived from known thioesterase activity genes, flanked by fluorescing molecules and/or quenching molecules, such as those described above, can be utilized. Labeled substrates can also be utilized in screening assays.

In another aspect of the present invention, screening using a fluorescent analyzer which requires single cell detection, such as a FACS machine, is utilized as a high throughput method to screen specific types of filamentous bacteria and fungi which form myceliates, such as Actinomyces or Streptomyces. In particular, screening is performed on filamentous fungi and bacteria which have, at one stage of their life cycle, unicells or monocells (multinucleoid cells fragment to produce monocells). Typically, spores of myceliate organisms germinate to make substrate mycelia (during which phase antibiotics are potentially produced), which then form arial mycelia. Arial mycelia eventually fragment to make more spores. Any filamentous bacteria or fungi which forms monocells during one stage of its life cycle can be screened for an activity of interest. Previously, this was not done because a branching network of multinucleoid (fungal like) cells forms with certain species. In a preferred embodiment, the present invention presents a particular species, *Streptomyces venezuelae*, for screening utilizing a fluorescent analyzer which requires single cell detection. The method of the present invention allows one to perform high throughput screening of myceliates for production of, for example, novel small molecules and bioactives. These cell types can be recombinant or non-recombinant.

*Streptomyces venezuelae*, unlike most other Streptomyces species, has been shown to sporulate in liquid growth culture. In some media, it also fragments into single cells when the cultures reach the end of vegetative growth. Because the production of most secondary metabolites, including bioactive small molecules, occurs at the end of log growth, it is possible to screen for *Streptomyces venezuelae* fragmented cells that are producing bioactivites by a fluorescence analyzer, such as a FACS machine, given the natural fluorescence of some small molecules.

In one aspect of the present invention, any *Streptomyces* or *Actinomyces* species that can be manipulated to produce single cells or fragmented mycelia is screened for a characteristic of interest. It is preferable to screen cells at the stage in their life cycle when they are producing small molecules for purposes of the present invention.

A fluorescence-based method for the selection of recombinant plasmids has been reported (BioTechniques 19:760–764, November 1995). *Escherichia coli* strains containing plasmids for the overexpression of the gene encoding uroporphyrinogen III methyltransferase accumulate fluorescent porphyrinoid compounds, which, when illuminated with ultraviolet light, causes recombinant cells to fluoresce with a bright red color. Replacement or disruption of the gene with other DNA fragments results in the loss of enzymatic activity and nonfluorescent cells.

Uroporphyrinogen III methyltransferase is an enzyme that catalyzes the S-adenosyl-1-methionine (SAM)-dependent addition of two methyl groups to uroporphyrinogen III methyltransferase to yield dihydrosirohydro-chlorin necessary for the synthesis of siroheme, factor F430 and vitamin B12. The substrate for this enzyme, uroporphyrinogen III (derived from ȳ-aminolevulinic acid) is a ubiquitous compound found not only in these pathways, but also in the pathways for the synthesis of the other so-called "pigments of life", heme and chlorophyll. Dihydrosirohydrochlorin is oxidated in the cell to produce a fluorescent compound sirohydochlorin (Factor II) or modified again by uroporphyrinogen III methyltransferase to produce trimethylpyrrocorphin, another fluorescent compound. These fluorescent compounds fluoresce with a bright red to red-orange color when illuminated with UV light (300 nm).

Bacterial uroporphyrinogen III methylases have been purified from E. coli (1), Pseudomonas (2), Bacillus (3) and Methanobacterium (4). A Bacillus stearothermophilus uroporphyrinogen III methylase has been cloned sequenced and expressed in E. coli (Biosci Biotechnol Biochem 1995 Oct.; 59(10):1817–1824).

In the method of the present invention, the fluorescing properties of this and other similar compounds are utilized to screen for compounds of interest, as described previously, or are utilized to enrich for the presence of compounds of interest. Host cells expressing recombinant clones potentially encoding gene pathways are screened for fluorescing properties. Thus, cells producing fluorescent proteins or metabolites can be identified. Pathway clones expressed in E. coli or other host cells, can yield bioactive compounds or "backbone structures" to bioactive compounds (which can subsequently be "decorated" in other host cells, for example, in metabolically rich organisms). The "backbone structure" is the fundamental structure that defines a particular class of small molecules. For example, a polyketide backbone will differ from that of a lactone, a glycoside or a peptide antibiotic. Within each class, variants are produced by the addition or subtraction of side groups or by rearrangement of ring structures ("decoration" or "decorated"). Ring structures present in aromatic bioactive compounds are known in some instance to yield a fluorescent signal, which can be utilized to distinguish these cells from the population. Certain of these structures can also provide absorbance characteristics which differ from the background absorbance of a non-recombinant host cell, and thus can allow one to distinguish these cells from the population, as well. Recombinant cells potentially producing bioactive compounds or "backbone" structures can be identified and separated from a population of cells, thus enriching the population for desirable cells. Thus, the method of the present invention also facilitates the discovery of novel aromatic compounds encoded by gene pathways, for example, encoded by polyketide genes, directly from environmental or other samples.

Compounds can also be generated via the modification of host porphyrin-like molecules by gene products derived from these samples. Thus, one can screen for recombinant clone gene products which modify a host porphyrin-like compound to make it fluoresce.

In yet another aspect of the present invention, cells expressing molecules of interest are sorted into 96-well or 384-well plates, specifically for further downstream manipulation and screening for recombinant clones. In this aspect of the present invention, the a fluorescence analyzer, such as a FACS machine is employed not to distinguish members of and evaluate populations or to screen as previously published, but to screen and recover positives in a manner that allows further screens to be performed on samples selected. For example, typical stains used for enumeration can affect cell viability, therefore these types of stains were not employed for screening and selecting for further downstream manipulation of cells, specifically for the purpose, for example, of recovering nucleic acid which encodes an activity of interest. In particular, cells containing recombinant clones can be identified and sorted into multi-well plates for further downstream manipulation. There are various ways of screening for the presence of a recombinant clone in a cell. Genes encoding fluorescent proteins, such as green fluorescent protein (Biotechniques 19(4):650–655, 1995), or the gene encoding uroporphyrinogen III methyltransferase (BioTechniques 19:760–764, November 1995) can be utilized in the method of the present invention as reporters to allow detection of recombinant clones. Recombinant clones are sorted for further downstream screening for an activity of interest. Screening may be for an enzyme, for example, or for a small molecule, and may be performed using any variety of methods, including those described or referred to herein.

In yet another aspect of the present invention, desirable existing compounds are modified, and evaluated for a more desirable compound. Existing compounds or compound libraries are exposed to molecules generated via the expression of small or large insert libraries generated in accordance with the methods described herein. Desirable modifications of these existing compounds by these molecules are detected and better lead compounds are screened for utilizing a fluorescence analyzer, such as a FACS machine. For example, E. coli cells expressing clones yielding small molecules are exposed to one or more existing compounds, which are subsequently screened for desirable modifications. Alternatively, cells are co-encapsulated with one or more existing compounds, and screened simultaneously to identify desirable modifications to the compound. Examples of modifications include covalent or non-covalent modifications. Covalent modifications include incorporation, transfer and cleavage modifications, such as the addition or transfer of methyl groups or phosphate groups to a compound, or the cleavage of a peptide or other bond to yield an active compound. Non-covalent modifications include conformational changes made to a molecule via addition or disruption of, for example, hydrogen bonds, ionic bonds, and/or Van der Wals forces. Modified compounds can be screened by various means, including those described herein.

Alternatively, existing compounds are utilized to modify the molecules generated via the expression of large or small insert clones, and desirable modifications of the molecules are screened for via fluorescence screening, utilizing various methods, including those described herein.

In another aspect of the present invention, molecules derived from expressed clones are exposed to organisms to enrich for potential compounds which cause growth inhibition or death of cells. For example, cultures of Staphylococcus aureus are co-encapsulated with compounds generated via expression of clones, or with cells expressing clones, and allowed to grow for a period of time by exposure to select media. Co-encapsulated products are then stained and screened for via fluorescence screening. Stains which allow detection of live cells can be utilized, allowing positives, which in this case would have no fluorescence, to be recovered. Alternatively, forward and side scatter characteristics are used to enrich for positives. Less or no growth of Staphylococus or other organisms being evaluated will yield capsules with less forward and/or side scatter.

In another aspect of the present invention clones expressing useful bioactivities are screened in-vivo. In this aspect, host cells are stimulated to internalize recombinant cells, and used to screen for bioactivities generated by these recombinant cells which can cause host cell death or modify an internal molecule or compound within the host.

Many bacterial pathogens survive in phagocytes, such as macrophages, by coordinately regulating the expression of a wide spectrum of genes. A microbes ability to survive killing by phagocytes correlates with its ability to cause disease. Hence, the identification of genes that are preferentially transcribed in the intracellular environment of the host is central to understanding of how pathogenic organisms mount successful infection.

Valdivia and Falkow have reported a selection methodology to identify genes from pathogenic organisms that are induced upon association with host cells or tissues. The group noted that fourteen *Salmonella typhimuium* genes, under control of at least four independent regulatory circuits, were identified to be selectively induced in host macrophages. The methodology is based on differential fluorescence induction (DFI) for the rapid identification of bacterial genes induced upon association with host cells that would work independently of drug susceptibility and nutritional requirements.

Differential fluorescence induction is employed in one aspect of the present invention to screen macrophages harboring bacterial clones carrying any virulence gene fused to a reporter molecule and a clone of a putative bioactive pathway. Macrophage cells are coinfected in the method of the present invention with clones of pathways potentially encoding useful bioactives, and plasmids or other vectors encoding virulence factors. Thus, one aspect of the present invention allows one to screen recombinant bioactive molecules that inhibit transcriptionally active reporter gene fusions in macrophage or other phagocyte cells. Bioactive molecules which inhibit virulence factors in-vivo are identified via a lack of expression of the reporter molecule, for example red or green fluorescent proteins. This method allows for the rapid screening for pathways encoding bioactive compounds specifically inhibiting a virulence factor or other gene product. Thus the screen allows one to identify biologically relevant molecules active in mammalian cells.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

DNA Isolation and Library Construction

The following outlines the procedures used to generate a gene library from an environmental sample.

DNA Isolation.

DNA is isolated using the IsoQuick Procedure as per manufacturer's instructions (Orca, Research Inc., Bothell, Wash.). DNA can be normalized according to Example 2 below. Upon isolation the DNA is sheared by pushing and pulling the DNA through a 25 G double-hub needle and a 1-cc syringes about 500 times. A small amount is run on a 0.8% agarose gel to make sure the majority of the DNA is in the desired size range (about 3–6 kb).

Blunt-Ending DNA.

The DNA is blunt-ended by mixing 45 $\mu$l of 10 X Mung Bean Buffer, 2.0 $\mu$l Mung Bean Nuclease (150 u/$\mu$l) and water to a final volume of 405 $\mu$l. The mixture is incubate at 37° C. for 15 minutes. The mixture is phenol/chloroform extracted followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentrifuge. Following centrifugation the DNA is dried and gently resuspended in 26 $\mu$l of TE buffer.

Methylation of DNA.

The DNA is methylated by mixing 4 $\mu$l of 10 X EcoR I Methylase Buffer, 0.5 $\mu$l SAM (32 mM), 5.0 $\mu$l EcoR I Methylase (40 u/$\mu$l) and incubating at 37° C., 1 hour. In order to insure blunt ends, add to the methylation reaction: 5.0 $\mu$l of 100 mM $MgCl_2$, 8.0 $\mu$l of dNTP mix (2.5 mM of each dGTP, dATP, dTTP, dCTP), 4.0 $\mu$l of Klenow (5 u/$\mu$l) and incubate at 12° C. for 30 minutes.

After 30 minutes add 450 $\mu$l 1xSTE. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation.

The DNA is ligated by gently resuspending the DNA in 8 $\mu$l EcoR I adaptors (from Stratagene's cDNA Synthesis Kit), 1.0 $\mu$l of 10 X Ligation Buffer, 1.0 $\mu$l of 10 mM rATP, 1.0 $\mu$l of T4 DNA Ligase (4 Wu/$\mu$l) and incubating at 4° C. for 2 days. The ligation reaction is terminated by heating for 30 minutes at 70° C.

Phosphorylation of Adaptors.

The adaptor ends are phosphorylated by mixing the ligation reaction with 1.0 $\mu$l of 10 X Ligation Buffer, 2.0 $\mu$l of 10 mM rATP, 6.0 $\mu$l of $H_2O$, 1.0 $\mu$l of polynucleotide kinase (PNK) and incubating at 37° C. for 30 minutes. After 30 minutes 31 $\mu$l $H_2O$ and 5 ml 10 X STE are added to the reaction and the sample is size fractionate on a Sephacryl S-500 spin column. The pooled fractions (1–3) are phenol/chloroform extracted once followed by an additional chloroform extraction. The DNA is precipitated by the addition of ice cold ethanol on ice for 10 minutes. The precipitate is pelleted by centrifugation in a microfuge at high speed for 30 minutes. The resulting pellet is washed with 1 ml 70% ethanol, repelleted by centrifugation and allowed to dry for 10 minutes. The sample is resuspended in 10.5 $\mu$l TE buffer. Do not plate. Instead, ligate directly to lambda arms as above except use 2.5 $\mu$l of DNA and no water.

Sucrose Gradient (2.2 ml) Size Fractionation.

Stop ligation by heating the sample to 65° C. for 10 minutes. Gently load sample on 2.2 ml sucrose gradient and centrifuge in mini-ultracentrifuge at 45 K, 20° C. for 4 hours (no brake). Collect fractions by puncturing the bottom of the gradient tube with a 20 G needle and allowing the sucrose to flow through the needle. Collect the first 20 drops in a Falcon 2059 tube then collect 10 1-drop fractions (labeled 1–10). Each drop is about 60 $\mu$l in volume. Run 5 $\mu$l of each fraction on a 0.8% agarose gel to check the size. Pool fractions 1–4 (about 10–1.5 kb) and, in a separate tube, pool fractions 5–7 (about 5–0.5 kb). Add 1 ml ice cold ethanol to precipitate and place on ice for 10 minutes. Pellet the precipitate by centrifugation in a microfuge at high speed for 30 minutes. Wash the pellets by resuspending them in 1 ml 70% ethanol and repelleting them by centrifugation in a microfuge at high speed for 10 minutes and dry. Resuspend each pellet in 10 $\mu$l of TE buffer.

Test Ligation to Lambda Arms.

Plate assay by spotting 0.5 $\mu$l of the sample on agarose containing ethidium bromide along with standards (DNA samples of known concentration) to get an approximate concentration. View the samples using UV light and estimate concentration compared to the standards. Fraction 1–4=>1.0 µg/µl. Fraction 5–7=500 ng/µl.

Prepare the following ligation reactions (5 ml reactions) and incubate 4° C., overnight:

| Sample | H$_2$O | 10X Ligase Buffer | 10 mM rATP | Lambda arms (ZAP) | Insert DNA | T4 DN Ligase Wu/(1) |
|---|---|---|---|---|---|---|
| Fraction 1-4 | 0.5 ml | 0.5 ml | 0.5 ml | 1.0 ml | 2.0 ml | 0.5 ml |
| Fraction 5-7 | 0.5 ml | 0.5 ml | 0.5 ml | 1.0 ml | 2.0 ml | 0.5 ml |

Test Package and Plate.

Package the ligation reactions following manufacturer's protocol. Stop packaging reactions with 500 µl SM buffer and pool packaging that came from the same ligation. Titer 1.0 µl of each pooled reaction on appropriate host (OD$_{600}$=1.0)[XLI-Blue MRF]. Add 200 µl host (in mM MgSO$_4$) to Falcon 2059 tubes, inoculate with 1 µl packaged phage and incubate at 37° C. for 15 minutes. Add about 3 ml 48° C. top agar [50 ml stock containing 150 µl IPTG (0.5 M) and 300 µl X-GAL (350 mg/ml)] and plate on 100 mm plates. Incubate the plates at 37° C., overnight.
Amplification of Libraries (5.0×10$^5$ Recombinants from each Library).

Add 3.0 ml host cells (OD$_{600}$=1.0) to two 50 ml conical tube and inoculate with 2.5 X 10$^5$ pfu of phage per conical tube. Incubate at 37° C. for 20 minutes. Add top agar to each tube to a final volume of 45 ml. Plate each tube across five 150 mm plates. Incubate the plates at 37° C. for 6–8 hours or until plaques are about pin-head in size. Overlay the plates with 8–10 ml SM Buffer and place at 4° C. overnight (with gentle rocking if possible).
Harvest Phage.

Recover phage suspension by pouring the SM buffer off each plate into a 50-ml conical tube. Add 3 ml of chloroform, shake vigorously and incubate at room temperature for 15 minutes. Centrifuge the tubes at 2 K rpm for 10 minutes to remove cell debris. Pour supernatant into a sterile flask, add 500 µl chloroform and store at 4° C.
Titer Amplified Library.

Make serial dilutions of the harvested phage (for example, 10$^{-5}$=1 µl amplified phage in 1 ml SM Buffer; 10$^{-6}$=1 µl of the 10$^{-3}$ dilution in 1 ml SM Buffer). Add 200 µl host (in 10 mM MgSO$_4$) to two tubes. Inoculate one tube with 10 µl 10$^{-6}$ dilution (10$^{-5}$). Inoculate the other tube with 1 µl 10$^{-6}$ dilution (10$^{-6}$). Incubate at 37° C. for 15 minutes. Add about 3 ml 48° C. top agar [50 ml stock containing 150 µl IPTG (0.5 M) and 375 µl X-GAL (350 mg/ml)] to each tube and plate on 100 mm plates. Incubate the plates at 37° C., overnight.

Excise the ZAP II library to create the pBLUESCRIPT library according to manufacturers protocols (Stratagene).

EXAMPLE 2

Normalization

Prior to library generation, purified DNA can be normalized. DNA is first fractionated according to the following protocol. A sample composed of genomic DNA is purified on a cesium-chloride gradient. The cesium chloride (Rf=1.3980) solution is filtered through a 0.2 µm filter and 15 ml is loaded into a 35 ml OptiSeal tube (Beckman). The DNA is added and thoroughly mixed. Ten micrograms of bis-benzimide (Sigma; Hoechst 33258) is added and mixed thoroughly. The tube is then filled with the filtered cesium chloride solution and spun in a VTi50 rotor in a Beckman L8-70 Ultracentrifuge at 33,000 rpm for 72 hours. Following centrifugation, a syringe pump and fractionator (Brandel Model 186) are used to drive the gradient through an ISCO UA-5 UV absorbance detector set to 280 nm. Peaks representing the DNA from the organisms present in an environmental sample are obtained. Eubacterial sequences can be detected by PCR amplification of DNA encoding rRNA from a 10-fold dilution of the *E. coli* peak using the following primers to amplify:

Forward Primer:
5'-AGAGTTTGATCCTGGCTCAG-3'    SEQ ID NO. 1

Reverse Primer:
5'-GGTTACCTTGTTACGACTT-3'    SEQ ID NO. 2

Recovered DNA is sheared or enzymatically digested to 3–6 kb fragments. Lone-linker primers are ligated and the DNA is sized selected. Size-selected DNA is amplified by PCR, if necessary.

Normalization is then accomplished as follows by resuspending double-stranded DNA sample in hybridization buffer (0.12 M NaH$_2$PO$_4$, pH 6.8/0.82 M NaCl/1 mM EDTA/0.1% SDS). The sample is overlaid with mineral oil and denatured by boiling for 10 minutes. Sample is incubated at 68° C. for 12–36 hours. Double-stranded DNA is separated from single-stranded DNA according to standard protocols (Sambrook, 1989) on hydroxyapatite at 60° C. The single-stranded DNA fraction is desalted and amplified by PCR. The process is repeated for several more rounds (up to 5 or more).

EXAMPLE 3

Cell Staining Prior to FACS Screening

Gene libraries, including those generated as described in Example 1, can be screened for bioactivities of interest on a FACS machine as indicated herein. A screening process begins with staining of the cells with a desirable substrate according to the following example.

A gene library is made from the hyperthermophilic archaeon *Sulfulobus solfataricus* in the λ-ZAPII vector according to the manufacturers instructions (Stratagene Cloning Systems, Inc., La Jolla, Calif.), and excised into the pBLUESCRIPT plasmid according to the manufacturers instructions (Stratagene). DNA was isolated using the Iso-Quick DNA isolation kit according to the manufacturers instructions (Orca, Inc., Bothell, Wash.).

To screen for β-galactosidase activity, cells are stained as follows. Cells are cultivated overnight at 37° C. in an orbital shaker at 250 rpm. Cells are centrifuged to collect about 2×10$^7$ cells (0.1 ml of the culture), resuspended in 1 ml of deionized water, and stained with C$_{12}$-Fluoroscein-Di- (-D-galactopyranoside (FDG). Briefly, 0.5 ml of cells are mixed with 50 µl C$_{12}$-FDG staining solution (1 mg C$_{12}$-FDG in 1 ml of a mixture of 98% H$_2$O, 1% DMSO, 1% EtOH) and 50 µl Propidium iodide (PI) staining solution (50 µg/ml of distilled water). The sample is incubated in the dark at 37° C. with shaking at 150 rpm for 30 minutes. Cells are then heated to 70° C. for 30 minutes (this step can be avoided if sample is not derived from a hyperthermophilic organism).

EXAMPLE 4

Figure 5:
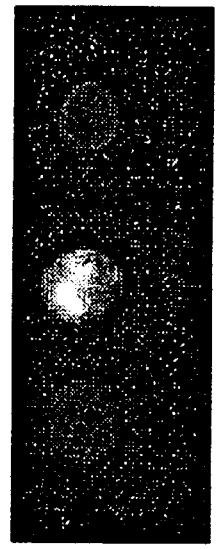
FIG. 5 shows β-galactosidase clones stained with three different substrates fluorescein-di-β-D-galactopyranoside (FDG), C12-fluorescein-di-β-D-galactopyranoside (C12FDG), chloromethyl-fluorescein-di-β-D-galactopyranoside (CMFDG). E. coli expressing β-galactosidase from Sulfulobus sulfotaricus species was grown overnight. Cells were centrifuged and substrate was loaded with deionized water. After five (5) minutes cells were centrifuged and transferred into HEPES buffer and heated to 70° C. for thirty (30) minutes. Cells were spotted onto a slide and exposed to UV light. This illustrates the results of the experiments described in Example 3.

Screening of Expression Libraries by FACS and Recovery of Genetic Information of Sorted Organisms The excised λ-ZAP II library is incubated for 2 hours and induced with IPTG. Cells are centrifuged, washed and stained with the desired enzyme substrate, for example $C_{12}$-Fluoroscein-Di-(-D-galactopyranoside (FDG) as in Example 3. Clones are sorted on a commercially available FACS machine, and positives are collected. Cells are lysed according to standard techniques (Current Protocols in Molecular Biology, 1987) and plasmids are transformed into new host by electroporation using standard techniques. Transformed cells are plated for secondary screening. The procedure is illustrated in FIG. 5. Sorted organisms can be grown and plated for secondary screening.

EXAMPLE 5

Sorting Directly on Microtiter Plates

Cells can be sorted in a FACS instrument directly on microtiter plates in accordance with the present invention. Sorting in this fashion facilitates downstream processing of positive clones.

Figure 6:
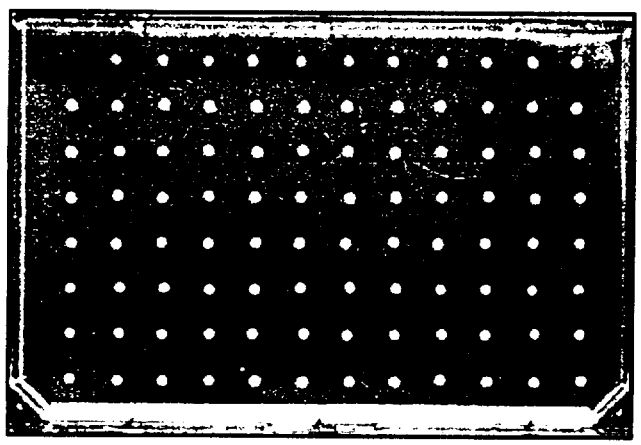
FIG. 6 shows a microtiter plate where E. coli cells sorted in accordance with the invention are dispensed, one cell per well and grown up as clones which are then stained with fluorescein-di-β-D-galactopyranoside (FDG) (10 mM). This illustrates the results of the experiments described in Example 5.

E. coli cells containing β-galactosidase genes are exposed to a staining solution in accordance with Example 3. These cells are then left to sit on ice for three minutes. For the cell sorting procedure they are diluted 1:100 in deionized water or in Phosphate Buffered Saline solution according to the manufacturers protocols for cell sorting. The cells are then sorted by the FACS instrument into microtiter plates, one cell per well. The sorting criteria is fluorescein fluorescence indicating β-galactosidase activity or PI for indicating the staining of dead cells (unlike viable cells, dead cells have no membrane potential; hence PI remains in the cell with dead cells and is pumped out with live cells). Results as observed on the microtiter plate are shown in FIG. 6.

TABLE 1

| Habitat | Cultured (%) |
| --- | --- |
| Seawater | 0.001–0.1 |
| Freshwater | 0.25 |
| Mesotrophic lake | 0.01–1.0 |
| Unpolluted esturine waters | 0.1–3.0 |
| Activated sludge | 1.0–15.0 |
| Sediments | 0.25 |
| Soil | 0.3 |

EXAMPLE 6

Production of Single Cells or Fragmented Mycelia

Inoculate 25 ml MYME media (see recipe below) in 250 ml baffled flask with 100 μl of *Streptomyces* 10712 spore suspension and incubated overnight @ 30° C. 250 rpm. After 24 hour incubation, transfer 10 ml to 50 ml conical polypropylene centrifuge tube and centrifuge @ 4,000 rpm for 10 minutes @ 25° C. Decant supernatant and resuspend pellet in 10 ml 0.05 M TES buffer. Sort cells into MYM agar plates (sort 1 cell per drop, 5 cells per drop, 10 cells per drop) and incubate plates @ 30° C.

MYME media (Yang, et. al., 1995 J. Bacteriol. 177(21): 6111–6117) contains: 10.3% sucrose, 1% maltose, 0.5% peptone, 0.3% yeast extract, 0.3% maltose extract, 5 mM MgC12 and 1% glycine

CITED LITERATURE

Alting-Mees, M. A., Short J. M., *Nucl. Acids. Res.* 1989, 17, 9494.
Hay, B. and Short, J. *Strategies*, 1992, 5, 16.
Enzyme Systems Products, Dublin Calif. 94568; Molecular Probes, Eugene, Oreg. 97402, Peninsula Laboratories, Belmont, Calif. 94002.
Adams, M. W. W., Kelly, R. M., *Chemical and Engineering News*, 1995, December 18.
Amann, R., Ludwig, W., and Schleifer, K.-H. *Microbiological Reviews*, 1995, 59, 143.Barnes, S. M., Fundyga, R. E., Jeffries, M. W. and Pace, N. R. *Proc. Nat. Acad. Sci. USA*, 1994, 91, 1609.Bateson M. M., Wiegel, J., Ward, D. M., *System. Appl. Microbiol.* 1989, 12, 1–7 Betz, J. W., Aretz, W., Hartel, W., *Cytometry*, 1984, 5, 145–150 Davey, H. M., Kell, D. B., *Microbiological Reviews*, 1996, 60, 4, 641–696 Diaper, J. P., Edwards, C., *J. Appl. Bacteriol.*, 1994, 77, 221–228 Enzyme Nomenclature, *Academic Press: NY*, 1992. Faber, Biotransformation in organic chemistry 2nd edition, Springer Verlag, 1995.Faber, U.S. Tonkovich and Gerber, Dept. of Energy Study, 1995.Fiering, S. N., Roeder, M., Nolan, G. P., Micklem, D. R., Parcks, D. R., Herzenberg, L. A. *Cytometry*, 1991, 12, 291–301.Giovannoni, S. J., Britschgi, T. B., Mover, C. L., Field, K. G., Nature, 1990 345, 60–63 Murray, M. G., and Thompson, W. F., *Nucl. Acids Res.*, 1980, 8, 4321–4325 Nolan, G. P., Fiering, S., Nicolas, J., F., Herzenberg, L. A., *Proc. Natl. Acad. Sci. USA*, 1988, 85, 2603–2607.Plovins A., Alvarez A. M., Ibanez M., Molina M., Nombela C., Appl. Environ. Microbiol., 1994, 60, 4638–4641. Short, J. M., Fernandez, J. F. Sorge, J. A., and Huse, W. *Nucleic Acids Res.*, 1988,16, 7583–7600.Short, J. M., and Sorge, J. A. *Methods in Enzymology*, 1992, 216, 495–508.Tonkovich, A., L., Gerber, M. A., US Department of Energy, Office of Industrial Technology, Biological and Chemical Technologies Research Program under contract DE-AC06-76RLO 1830 Torvsik, V. Goksoyr, J. Daae, F. L., *Appl. and Environm. Microbiol.* 1990, 56, 782–787 Wittrup, K. D., Bailey, J. E., Cytometry, 1988, 9, 394–404.Wrotnowski, *Genetic Engeneering News*, 1997, February 1.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed is:

1. A method for identifying bioactivities or biomolecules produced by a mycelia comprising:

growing a mycelia under conditions and for a time sufficient to allow the mycelia to produce a bioactivity or biomolecule that modifies a substrate molecule therein so as to cause fluorescence;

fragmenting said mycelia to produce monocells; and screening said monocells using a fluorescence analyzer to identify one or more bioactivity or biomolecule produced by the mycelia.

2. The method of claim 1, wherein the mycelia is a recombinant cell.

3. The method of claim 1, wherein the mycelia is a non-recombinant cell.

4. The method of claim 1, wherein the biomolecule is a secondary metabolite.

5. The method of claim 1, wherein the cell is a filamentous bacteria or fungi.

6. The method of claim 1, wherein the growth conditions include liquid culture.

7. The method of claim 1, wherein the fragmenting comprises centrifugation of the mycelia to produce the monocells.

8. The method of claim 3, wherein the cell is a Streptomyces.

9. The method of claim 8, wherein the Streptomyces is *Streptomyces venezuelae*.

10. A method for identifying bioactivities or biomolecules produced by a mycelia comprising:

growing a mycelia under conditions and for a time sufficient to allow the mycelia to produce a bioactivity or biomolecule that modifies a substrate molecule therein so as to cause fluorescence;

fragmenting said mycelia to produce monocells;

growing the monocells in an encapsulated system; and screening said encapsulated mycelia using a fluorescence analyzer to identify one or more bioactivity or biomolecule produced by the mycelia.

* * * * *